(12) United States Patent
Oravecz

(10) Patent No.: US 6,981,417 B1
(45) Date of Patent: Jan. 3, 2006

(54) SCANNING ACOUSTIC MICRO IMAGING METHOD AND APPARATUS FOR NON-RECTANGULAR BOUNDED FILES

(75) Inventor: Michael G. Oravecz, Naperville, IL (US)

(73) Assignee: Sonoscan, Inc., Elk Grove Village, IL (US)

( * ) Notice: Subject to any disclaimer, the term of this patent is extended or adjusted under 35 U.S.C. 154(b) by 0 days.

(21) Appl. No.: 10/423,450

(22) Filed: Apr. 25, 2003

Related U.S. Application Data

(60) Provisional application No. 60/376,042, filed on Apr. 26, 2002.

(51) Int. Cl.
 *G01N 29/06* (2006.01)
(52) U.S. Cl. .............. 73/619; 73/621; 73/612; 73/614; 73/629; 73/633; 73/634
(58) Field of Classification Search .......... 73/602, 73/606, 607, 609, 612, 614, 618, 619, 620, 73/621, 624, 625, 626, 627, 628, 629, 631, 73/633, 634, 640
See application file for complete search history.

(56) References Cited

U.S. PATENT DOCUMENTS

| | | | | |
|---|---|---|---|---|
| 3,496,764 A | * | 2/1970 | Stouffer ................... 600/445 |
| 4,131,021 A | * | 12/1978 | Mezrich et al. ............ 73/606 |
| 4,518,992 A | | 5/1985 | Kessler et al. ............ 348/163 |
| 4,781,067 A | | 11/1988 | Cichanski ................. 73/620 |
| 4,866,986 A | | 9/1989 | Cichanski ................. 73/600 |
| 5,331,962 A | * | 7/1994 | Coleman et al. ........... 600/444 |
| 5,372,042 A | * | 12/1994 | Jarman et al. ............. 73/588 |
| 5,408,881 A | * | 4/1995 | Piche et al. ............... 73/582 |
| 5,600,068 A | | 2/1997 | Kessler et al. ............ 73/620 |
| 5,627,320 A | * | 5/1997 | Moore ..................... 73/606 |
| 5,684,252 A | | 11/1997 | Kessler et al. ............ 73/618 |
| 6,055,861 A | * | 5/2000 | Banta et al. .............. 73/626 |
| 6,122,223 A | * | 9/2000 | Hossack ................... 367/11 |
| 6,357,136 B1 | | 3/2002 | Erickson et al. ............ 34/60 |
| 6,374,675 B1 | | 4/2002 | DePetrillo ................ 73/610 |
| 6,460,414 B1 | | 10/2002 | Erickson et al. ........... 73/603 |
| 6,500,118 B1 | | 12/2002 | Hashimoto ............... 600/437 |
| 2002/0058871 A1 | | 5/2002 | Oravecz et al. ........... 600/437 |
| 2003/0023393 A1 | | 1/2003 | Oravecz ................... 702/39 |
| 2004/0149021 A1 | | 8/2004 | Kessler et al. ............ 73/105 |

FOREIGN PATENT DOCUMENTS

JP    55072855 A   *   6/1980

(Continued)

OTHER PUBLICATIONS

Brouchure of Sonoscan, Inc., Sonomicroscope System 3100 C-Mode Scanning Acoustic Microscope (C-SAM), six (6) pages; Copyright 1988 Sonoscan, Inc.

(Continued)

*Primary Examiner*—Hezron Williams
*Assistant Examiner*—Rose M. Miller
(74) *Attorney, Agent, or Firm*—Welsh & Katz, Ltd.

(57) ABSTRACT

Method and implementing apparatus useful in acquiring data on acoustic features within a sample provides a pulsed acoustic probe and a stage system for effecting relative movement between the sample and the probe. The stage system is commanded such that the probe interrogates a non-rectangularly bounded space on the sample surface or within the volume of the sample. Acoustic energy reflected from or transmitted through the sample is sensed. Amplitude signals are developed from the sensed acoustic energy. Data characterizing the developed amplitude signals are stored for subsequent processing.

16 Claims, 29 Drawing Sheets

FOREIGN PATENT DOCUMENTS

| | | | |
|---|---|---|---|
| JP | 62293158 A | * | 12/1987 |
| JP | 10-277042 | | 10/1998 |
| JP | 411009604 A | | 1/1999 |
| RU | 2180111 C2 | * | 2/2002 |

OTHER PUBLICATIONS

Brochure of "The Virtual Sample", reprinted with revisions to format from the Feb. 2003 edition of Surface Mount Technology, copyright 2003 by Penn Well Corporation; Tom Adams and Lawrence W. Kessler (4 pages).

Survey Sheds Light on Irksome Die Cracks, Tom Adams; 1 Page (doublesided); Reprinted from the Aug. 1996 edition Solid State Technology—Copyright 1996 by Pennwell Publishing Company.

* cited by examiner

GENERAL SAMPLE

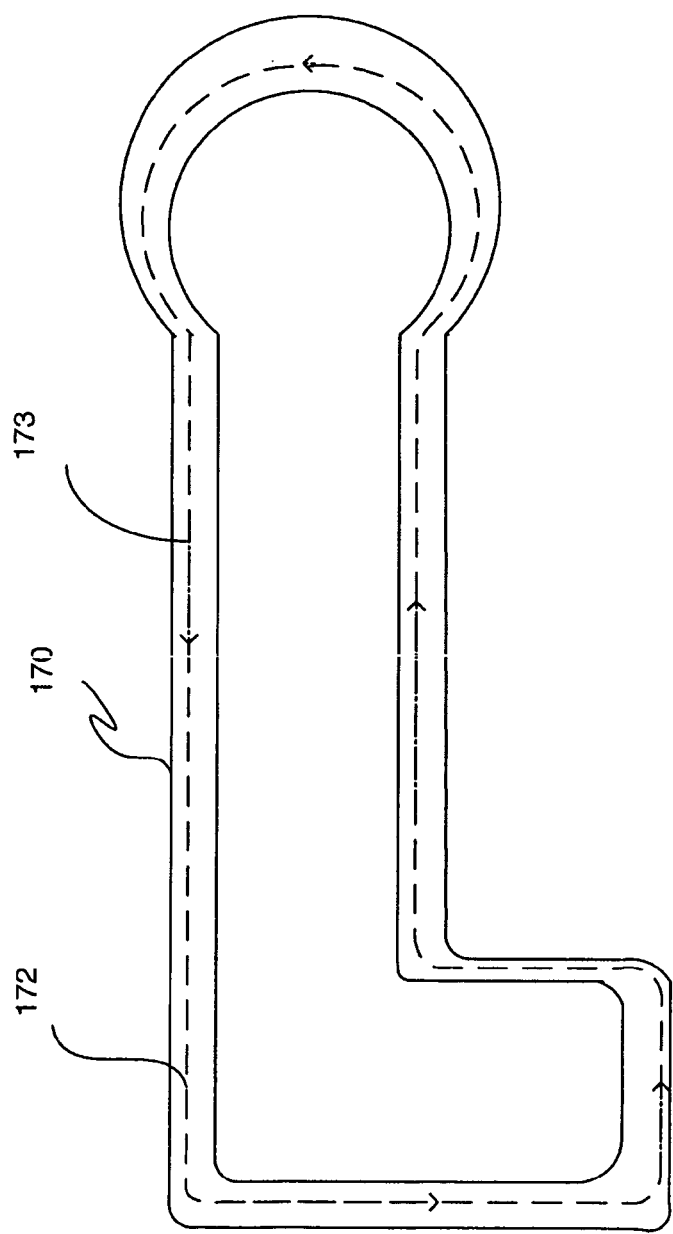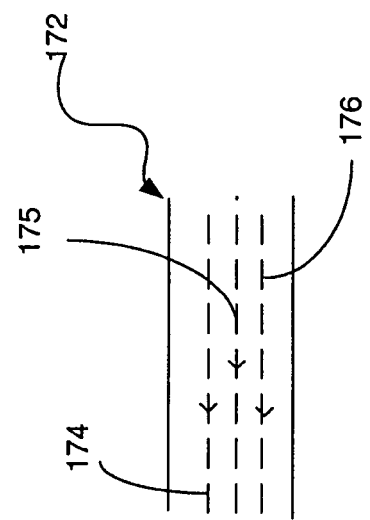
FIG. 21
FIG. 21A

FIG. 22A
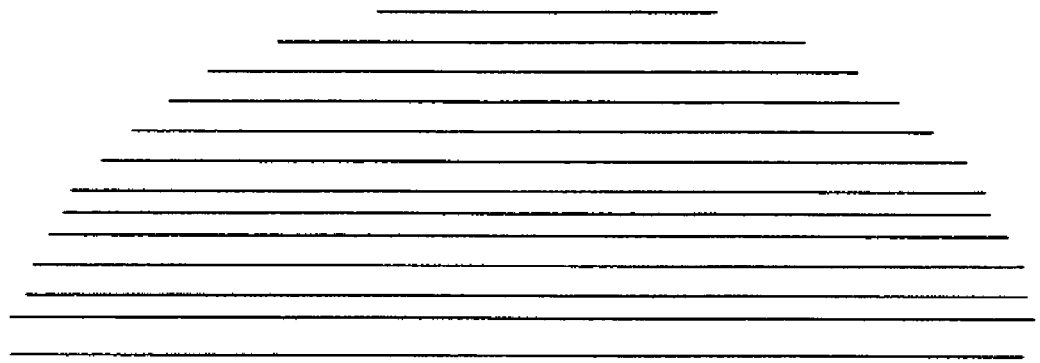
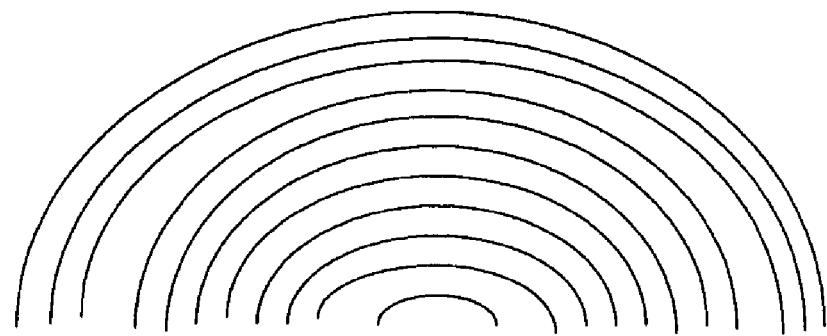
FIG. 22B

US 6,981,417 B1

SCANNING ACOUSTIC MICRO IMAGING METHOD AND APPARATUS FOR NON-RECTANGULAR BOUNDED FILES

RELATED APPLICATIONS

This application is related to, but not dependent upon, application Ser. No. 09/911,602, filed Jul. 24, 2001 for Acoustic Micro Imaging Method and Apparatus for Capturing 4D Acoustic Reflection Virtual Samples, and application Ser. No. 10/007,984, filed Nov. 13, 2001 for Frequency Domain Processing of Scanning Acoustic Micro Imaging Signals, both assigned to the assignee of the present invention.

BACKGROUND OF THE INVENTION

This invention concerns improvements in the field of non-destructive testing and failure analysis using pulsed ultrasound as a material probe. While many of the applications of the invention are useful in a broad range of applications, the invention will be described in the context of acoustic micro imaging ("AMI"). To further an understanding of the broad applicability of the principles of the invention, a brief description will be engaged of various scanning modes commonly employed today in AMI.

The most basic form of acoustic interrogation is illustrated in FIG. 1 in which an ultrasonic transducer 20 is excited with a sharp electrical pulse and emits a pulse of ultrasonic energy which is brought to a focus 22 within sample 24 by a lens (not shown) at the distal end of the transducer 20. FIG. 1A is intended to represent the sample 24 as having a front surface A, an internal interface (acoustic impedance mismatch), and a bottom surface C. An acoustic (sometimes termed herein "ultrasound") pulse is reflected from the front surface A, interior interface B and bottom surface C and sensed by the transducer 20.

The amplitude of the reflected acoustic waveform as a function of time is shown in highly simplistic form FIG. 1B. The waveform 26 is commonly known as the "A" waveform or "A-scan", and in practice contains a great deal of information about acoustic impedance perturbations or features in the body of the sample.

In waveform 26 the first spike 28 is the "main bang" resulting from the electrical excitation of the transducer 20. A second spike 30 occurs later in time and is the sensed reflection from front surface A of the sample body 24. Still later in time, the transducer senses a reflection 32 from the interface B, and finally a reflection 34 from the rear surface C of the sample body 24.

As will be described in more detail below, acoustic microscopes employ a time window or "gate" 36 which passes only returned reflections which lie within a certain span of time corresponding to a certain depth in the sample. In FIG. 1B gate 36 is set to pass only the signal representing interface B reflection 32.

FIG. 2 represents in highly schematic form the "C-Mode" scan wherein a focused image is formed of an X-Y plane at a specific depth in the Z axis. FIG. 2A is another illustration of a C-Mode scan, showing the A-scan waveform produced from an interrogation by transducer 42 of three different Points 1, 2, and 3 in the sample. At Point 1, the A waveform 44 shows a reflection 46 at the front surface and a smaller reflection from an interface 48 in the sample 50. A waveform 52 associated with X-Y Point 2 shows a reflection 54 from an air gap 56 formed in the interface 58. The reflection 54 shows a phase reversal because of the lower impedance of air than of the sample material. Waveform 59 associated with Point 3 reveals a small amplitude reflection 60 from what may be an occlusion 62 in the body of the sample 50. The polarity of the reflection 60, being the same as that of the first reflection 63, suggests that the reflection 60 is not from an air void or other feature having lower acoustic impedance than that of the sample material.

In C-Mode scanning, a gate is set, as shown at 43 in FIG. 2A, for example, within which a peak detector (not shown) detects the peak value of the gated signal segments. The peak values detected are stored in a 2D (spatial) X-Y memory (not shown).

In C-Mode scanning acoustic microscopy a focused spot of ultrasound is generated by an acoustic lens assembly at frequencies typically in the range of 10 MHz to 200 MHz or more. The ultrasound is conducted to the sample by a coupling medium, usually water or an inert fluid. The angle of the rays from the lens is generally kept small so that the incident ultrasound does not exceed the critical angle of refraction between the fluid coupling and the solid sample. The focal distance into the sample is shortened by the refraction at the interface between the fluid coupling and the solid sample.

The transducer alternately acts as sender and receiver, being electronically switched between transmit and receive modes. A very short acoustic pulse enters the sample, and return acoustic reflectances are produced at the sample surface and at specific impedance interfaces and other features within the sample. The return times are a function of the distance from the encountered impedance feature to the transducer and the velocity of sound in the sample material(s).

An oscilloscope display of the acoustic reflectance pattern (the A scan) will clearly show the depth levels of impedance features and their respective time-distance relationships from the sample surface.

This provides a basis for investigating anomalies at specific levels within a part (sometimes termed herein a "sample"). The gated acoustic reflectance amplitude is used to modulate a CRT that is one-to-one correlated with the transducer position to display reflectance information at a specific level in the sample corresponding to the position of the chosen gate in time.

With regard to the depth zone within a sample that is accessible by C-scan techniques, it is well known that the large acoustic reflectance from a liquid/solid interface (the top surface of the sample) masks the small acoustic reflectances that may occur near the surface within the solid material. This characteristic is known as the dead zone, and its size is usually of the order of a few wavelengths of sound.

Far below the surface, the maximum depth of penetration is determined by a number of factors, including the attenuation losses in the sample and the geometric refraction of the acoustic rays which shorten the lens focus in the solid material. Therefore, depending upon the depth of interest within a sample, a proper transducer and lens must be used for optimum results.

In C-Mode scanning acoustic microscopy ("C-SAM"), contrast changes compared to the background constitute the important information. Voids, cracks, disbonds, and other impedance features provide high contrast and are easily distinguished from the background. Combined with the ability to gate and focus at specific levels, C-SAM is a powerful tool for analyzing the nature of any acoustic impedance feature within a sample.

In this type of C-mode scanning, the A-scan for each point interrogated by the ultrasonic probe is discarded except for the image value(s) desired for that pixel. Two examples of image value data are: (a) the peak detected amplitude and polarity, or (b) the time interval from the sample's surface echo to an internal echo (the so-called "time-of-flight" of "TOF" data).

FIG. 3 illustrates the "B-Scan" mode which produces cross-section data displayed as amplitude values of digital samples of A-Scan waveforms arrayed in a simulated X-Z plane of the sample.

FIG. 4 is another mode related to the B-Scan mode and is termed by the assignee of this invention as the Quantitative B-Scan Analysis Mode, or "Q-BAM". A Q-BAM scan produces a calibrated cross-section of data in the X-Z plane of the sample. The data captured is caused to be completely in focus through the entire Z depth by scanning at various Z positions and readjusting the transducer focus before each successive scan. The position of the probe focus and the gate are automatically linked such that the gated segment of the waveform always represents reflections from impedance features which are in focus.

FIG. 5 illustrates a scan mode known as Three Dimensional Time-of-Flight or "3D TOF" which internally tracks first interface topography within a sample. Color-coded 3D graphic imagery is commonly employed to show the TOF topography of the inspected feature in relation to its distance from the top surface of the inspected sample.

FIG. 6 shows a transmission mode which investigates the entire thickness of the sample in one scan. It is the ideal scan mode for rapidly identifying gross anomalies such as a die disbond. The anomaly detected can later be isolated and inspected in detail with C-Mode analysis.

FIG. 7 represents a combination of reflection and transmission mode scanning. In one X-Y scan the entire thickness and a specific interface or anomaly can be inspected.

As represented schematically in FIG. 8, AMI is commonly employed to automatically position, focus, scan, analyze and report on acoustically detectable features in a tray of parts such as integrated circuits.

FIG. 9 shows a similar application for ultrasonically inspecting various parts or locations on a PC board. The process is designed to automatically examine multiple types of parts located at specific locations on the PC board.

FIG. 10 depicts a "bulk-scan" mode which provides two dimensional (X,Y) display and measurement of material properties throughout a predetermined gated thickness (Z depth) in the examined part.

Multi-Scan (FIG. 11) is a way to obtain multiple C-Mode images with one scan at preseleted interfaces, or obtain a C-Mode and Bulk-Scan image simultaneously. It is ideally suited for applications such as simultaneous overmold material and interface bond analysis FIG. 12 illustrates an "R-Scan" mode—a rotational scanner which locates hidden defects within the circumference of a cylindrical sample. Nondestructively it "unwraps" and displays two dimensional (X,theta) image from 0 to 360 degrees of rotation.

FIG. 13 illustrates a known technique in which a spherical sample is inspected for subsurface defects. The spherical sample is rotated about a polar axis while a probe is stepped along the circumference of the part in a plane intersecting the polar rotation axis. The probe is pulsed and an audible or visual indicator activated when an acoustic impedance reflection above a prescribed amplitude threshold is detected. The inspection data is not stored, nor even acquired.

FIG. 14 a screen print of a monitor image formed using a commercial C-Mode scanning acoustic microscope manufactured by the assignee of the present invention. The sample was an encapsulated integrated circuit having a die attached to a pad, with leads extending radially from all sides of the die.

As noted, the "time of flight" of the acoustic pulses from transducer to sample front surface was 20.50 microseconds. The front end ("FE") gain was set at 22.500 dB, and the slice gain at 26.000 dB. The gate was positioned at 0.736 microseconds from the front surface echo and had a width of 0.564 microseconds in order to capture a depth in the package embracing the die leads and the die-pad interface. The transducer frequency was 15 MHz and the transducer focal length was 0.774 inch.

Acoustic reflectance signals 66, 68, 70 were stimulated by the transducer at three location, numbered "1", "2", and "3", respectively. Location "1" was on a bonded lead. The white color in the image reproduction signifies a sound bond between the inspected lead and the encapsulating material. Corresponding acoustic reflectance signal 66 shows a reflection 72 from the front surface of the package. Less than 1 microsecond later, we see a positive polarity reflection 74 from the soundly bonded lead. As the reflection 74 is within the reproduction gate 76, the reflection 74 is rendered in the image 64.

However, with the probe at position "2" over a different lead, we see in acoustic reflectance signal 68 a negative polarity reflection 80, indicating that the acoustic wave encountered an interface with a lower acoustic impedance than that of the sample material. The logical interpretation of this data is that the lead at position "2" is disbanded and that the resulting air gap is responsible for the phase reversal of the reflection 80. Again, because the reflection 80 is within the gate, it is visualized in the image 64.

With the probe at position "3" on the die-pad interface, acoustic reflectance signal 70 shows a negative polarity reflection from the interface, indicating a die-pad disbond (air gap). The location of the reflection 82 closer to the front surface reflection 72 indicates that the die-pad interface is slightly higher (closer to the probe) than the leads at positions "1" and "2".

As described above, in conventional C-Mode AMI, the only data that is captured and stored for display and analysis is the peak value of the amplitude waveform within the gate 76, optionally along with polarity and TOF data.

Thus, from the above description it is known in the field of acoustic image microscopy to capture an X-Y set of data points, each point representing the detected peak of a gated region of an amplitude-modulated acoustic signal reflected from impedance features within the body of an insonified solid part. The set of data points may be visualized, for example on the screen of a computer monitor.

By moving the position of the gate along the time axis of the acoustic reflectance signal, a particular plane or layer within the examined part may be inspected. Referring to FIG. 15, this process "slices" the part into as many horizontal sections as desired. Typically 10 slices are adequate for thin samples such as integrated circuits, however, up to 200 slices can be made on commercially available AMI equipment. Equipment software can be set to divide the part into equal thickness slices. Each slice is then automatically scanned with the focus and gate optimized for each specific slice depth. As in C-Mode scanning, the reflectance signals are gated and peak amplitude values are stored. After scanning, the slices may be displayed simultaneously as "thumbnail" images on a computer monitor screen. Typically the slices are reviewed in detail or thumbnail images are reviewed in a slide show sequence—a process analogous to descending acoustically through the part or peeling it apart layer by layer.

The described equipment has software which assembles the slices and reconstructs the data into an "acoustic solid". The acoustic solid can be rotated to any desired angle of view. With this software, an operator can also visualize cross-sections of the acoustic solid. Sectioning can take many different forms—a single horizontal, vertical or diagonal section can be removed. Multiple sections or "bits" can be removed which are defined by material properties, rather than by geometry. For example, an operator might remove all of the molding compound from an IC package and still leave intact the image of a crack within the molding compound.

As described, the acoustic solids created by effectively stacking an array of such X-Y data sets have proven to be useful in certain applications where the information desired to be recorded and displayed is simply the signal peaks in the gated regions of interest. However, many applications exist wherein the information desired to be retrieved from the solid part is not precisely known at the time the part is acoustically interrogated. Since the acoustic reflectance signals returned from each pulse are lost, except for the peak of the signal within the gated region (and optionally, polarity and TOF data), it is not possible to derive additional information from the stored X-Y-Z data set of amplitude peak values. It is not possible off-line, for example, to adjust the position of the gate to change the depth of the inspected plane. Nor is it possible to employ signal processing analytics on the missing acoustic signal information to learn more about the anomalies which perturbed the insonifying sound pulses.

Another prior art approach employed in AMI, described in U.S. Pat. No. 6,032,534, differs from the above description in at least respect. One X-Y scan across a sample is employed with a transducer having a high F-number lens. The acoustic reflectance signal (A-scan) is captured, digitized, and stored as digital data. Because the capture gate may be as wide as the specimen (or the zone of interest) is deep, reflections from all levels in the specimen are stored. After capture of the ungated, full volume waveform, a gate (or multiple gates) can be introduced at any position to visualize reflecting features in a specimen at a depth and thickness corresponding to the gate location and width.

In this approach, the acoustic waveform for each pixel is saved to storage means (memory, hard drive, etc.). The number of samples in a stored waveform may vary depending on the application and any implementation specific limits. For example, 1 to 4 microseconds of the acoustic waveform, including and after the surface echo, may be stored. At a 1 GHz sampling rate, this would represent 1000 to 4000 samples per each pixel's acoustic waveform. The total number of pixels in an image depends on the chosen image resolution. Typical image resolutions include: 256×240, 512×480, and 1024×960. The total storage required grows rapidly as the resolution increases.

The last-described scan mode provides the data for a 2-dimensional B-scan. Depending upon the transducer, either all or only a small part of the stored waveform may be within the focused region of the ultrasonic beam. Or, depending upon the transducer and the sample, either all or only a small part of the sample's thickness may be covered by the stored waveform. Or, depending upon the transducer and the sample, either all or only a small part of the sample's thickness may be within the focused region of the ultrasonic beam.

The advantage of this approach is that the full acoustic reflectance waveform is captured and digitized for later review, gating and processing. No information is irretrievably discarded as in conventional C-Scan approach which employs gated peak detection and storage of gated signal peaks (which become the image pixels upon display), and, optionally polarity and time-of-flight data. As described, to produce a display of any particular level or levels within the sample, the gating is set for that level or levels.

One obvious and significant disadvantage of this approach, however, is that all images generated by changing gate position are not in sharp focus. An attempt is made to place the entire specimen depth in focus which means that no plane is in the sharpest possible focus. As will become evident from the ensuing description, another drawback of moment of this last-described approach is the limited amount of data that can be gathered in a single scan of the sample.

From the above description it can be understood that in the practice of conventional AMI, all inspection techniques utilize regular scanning of the acoustic probe across the sample, typically in rectangular rasters or fields. One minor departure from standard continuous XY rectangular scanning is in the scanning of trays of semiconductor parts where it is known to interrupt the acoustic beam in the interstitial areas between the semiconductor parts.

Also, as shown in FIG. 9, it is known to configure the motion controller for the XYZ stage to rectangular-raster scan various sized and shaped rectangular parts.

However, there are many applications wherein the target field desired to be scanned is not rectangular, and thus does not conform to the shape of the field scanned by conventional AMI equipment. One field in which a strong need has arisen for non-rectangular scanning AMI is medical and pharmaceutical packaging where hermetic sealing of drugs, medical instruments, and the like is desirable or mandatory. FIG. 15A schematically depicts a drug package 90 in which a pill (not shown) or other drug (dry or liquid) is encapsulated in a well 91 in a package body having a seal area 92. A plastic film bonded to the sealing area 92 hermetically seals the contents of the well 91.

FIG. 15B illustrates a medical instrument package 93 in which, as in FIG. 15A, the body of the package 93 defines a well 95 in which a surgical or other medical instrument (not shown) is hermetically sealed by means of a cover film bonded to a seal area 97.

A wide variety of defects within the seal or bond area of such packages can be inspected nondestructively using AMI technology. The defects amenable to AMI inspection include:

1) Voids within sealed layers. Voids in the adhesive or bond area can occur between layers, often weakening the intended seal.
2) Delaminations of sealed layers. Regions within layers that have separated from each other can weaken the seal and allow possible contamination routes.
3) Variation in seal width. Seal width can vary, the seal potentially becoming weaker where it is narrower.
4) Contaminant in seal area. Foreign material can become trapped or encased in the seal area, compromising the bond integrity.
5) Channel opens or "leakers". A defect or opening in the seal can allow contamination to enter, or the contents of the package to escape.
6) Material defects. The host material from which a package or device is constructed can contain inherent, internal defects that may ultimately affect the bond or seal quality. Examples are cracks, inclusions, thinning and other various anomalies.

Various package types are amenable to AMI inspection, including:
1) Bags and pouches,
2) Bottles and tubes,
3) Blister packages,
4) Devices,
5) Cartridges and cassettes, or
6) Sensors A variety of applicable packaging materials are conducive to AMI inspection techniques, including:
1) Adhesives,
2) Laminate foils and films,
3) Formed and molded devices,
4) Polymers,
5) Metals, and
6) Ceramics.

The use of conventional of XY raster scanning techniques to identify defects in seal areas is slow and inefficient. In FIG. 15A the application of a conventional XY raster scan, as shown at 99. It can be seen that the area around the seal area 92 to be inspected and the well 91 are also typically also scanned even though such is unnecessary. In some cases it may be undesirable to acoustically stimulate the contents of the well 91. Whereas it may be possible according to known practices to shut off the acoustic beam while passing over the well 91, for example, nevertheless the probe is forced to make its traditional, though wasteful, excursion across the well 91 to the limits of the sweep.

Similarly, an XY raster scan 101 of the entire medical device package 93 in FIG. 15B, as is conventional, when only the seal land is the target of inspection, is highly wasteful of AMI resources, and undesirably slow and expensive. In many applications, the need for the acquired data is urgent and the time required to detect and identify serious defects is therefore critical.

The need for a scanning AMI system capable of scanning arbitrary non-rectangular shapes is not limited to the sealing areas of packages, but has a large number of other applications, including the inspection of semiconductor devices, as will be explained below.

It is an object of the invention to provide scanning AMI methods and apparatus capable of scanning in two and three dimensions areas and three-dimensional volumes having non-rectangularly bounded areas and volumes.

It is another object of the invention in which such methods and apparatus are enhanced by additional features including 4D data capture, post processing of captured data, and three-dimensional data modeling.

BRIEF DESCRIPTION OF THE FIGURES

FIGS. 21–29 illustrate schematically various 2D and 3D scanning modes and techniques which may be employed in the practice of the present invention.

DESCRIPTION OF THE PREFERRED EMBODIMENTS

The method of the invention to be described may be beneficially employed in a scanning acoustic microscope having a pulsed ultrasonic probe and an XYZ (three axis) probe translation stage for translating the probe across a sample, or an XYZ sample translation stage for moving the sample relative to the probe.

4D Data Capture and Storage

Reviewing the various prior art scan modes illustrated in FIGS. 1–15 it will be understood that an A-scan (FIG. 1B, for example) can be thought of as representing reflection data in a time dimension for a single point in the sample examined—that is, reflection amplitude detected at the transducer as a function of time (time being associated with depth in the examined sample).

Throughout this application, reference is made to an A-scan as representing reflection data in a time dimension for a single point in the sample examined, or similar language. It is important to understand that this descriptive nomenclature is used for convenience. In actuality an A-scan represents reflection data in a time dimension for a single set of ultrasonic excitation conditions or parameters. These conditions or parameters include the location in the sample of the transducer focal point (point of smallest cross-sectional area of the probe waist), sometimes termed herein the "transducer focal point", "focal point", "point", "transducer focus", "focus", or other similar language. The set of excitation conditions also includes the probe spot size, ultrasound frequency and bandwidth, pulse height (energy), and transducer depth of field.

However, of these excitation conditions, the only one that is typically varied during the practice of the present invention is the location of the transducer focal point. The remaining conditions are held constant. For that reason, for ease of explanation of the present invention, when the application speaks of an A-scan representing reflection data for a single point in the examined sample (or similar language), it is to be understood that what is meant is reflection data corresponding to a particular set of excitation conditions, including the location of a single transducer focal point in the examined sample.

Figure 2:
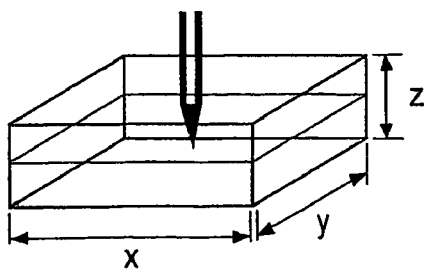
Figure 2A:
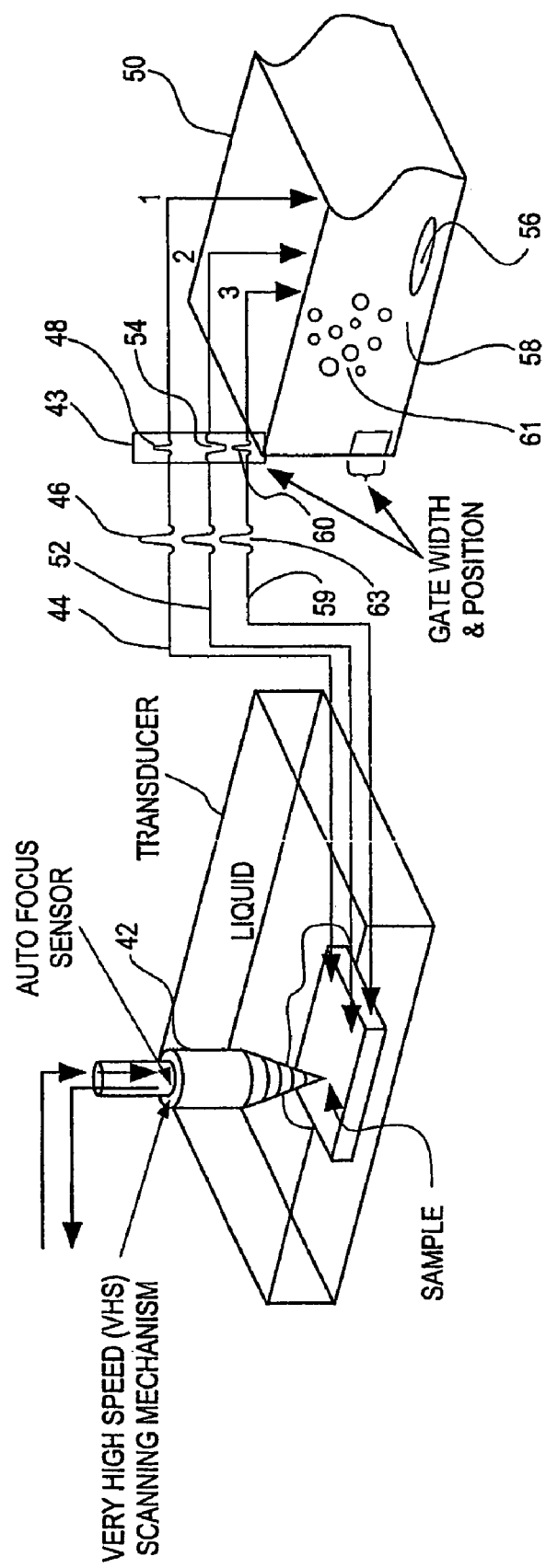
Figure 3:
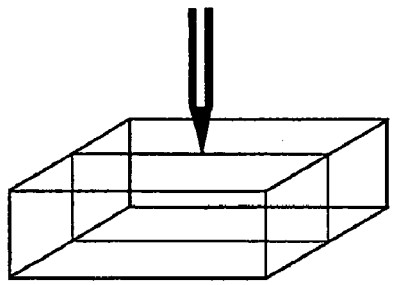
Figure 4:
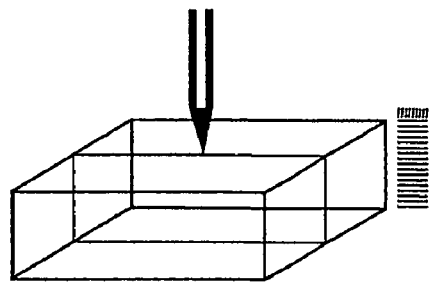
Figure 5:
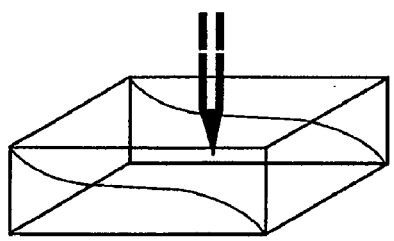
Figure 6:
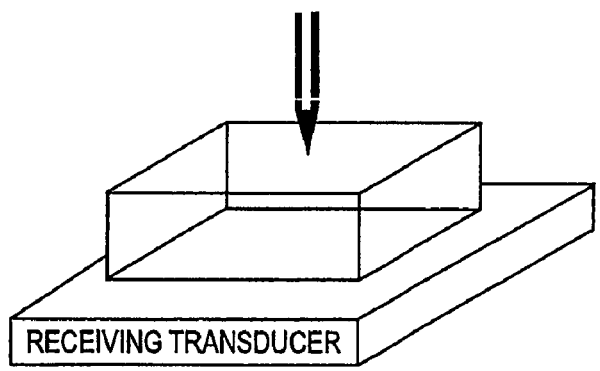
Figure 7:
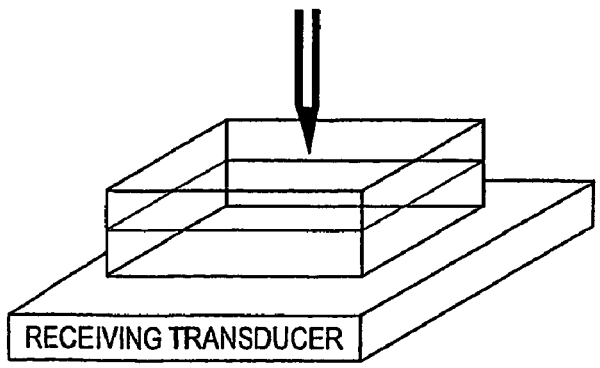
Figure 8:
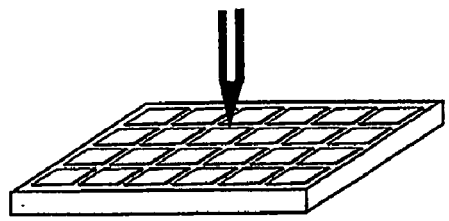
Figure 9:
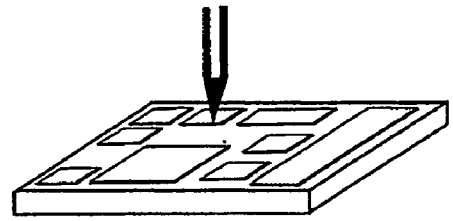
Figure 10:
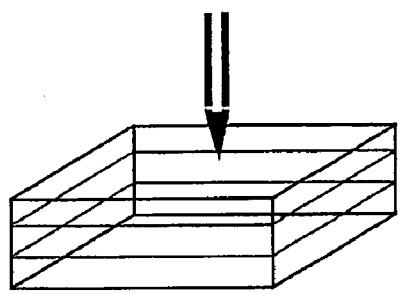
Figure 11:
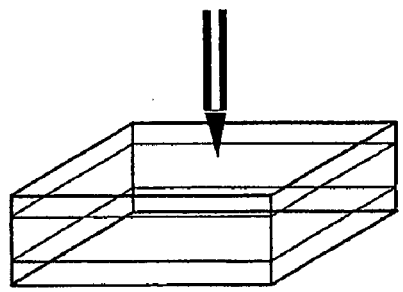
Figure 12:
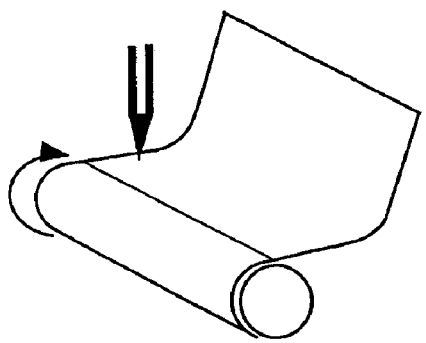
Figure 13:
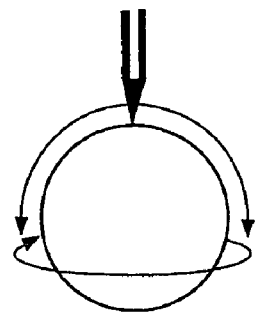
Figure 14:
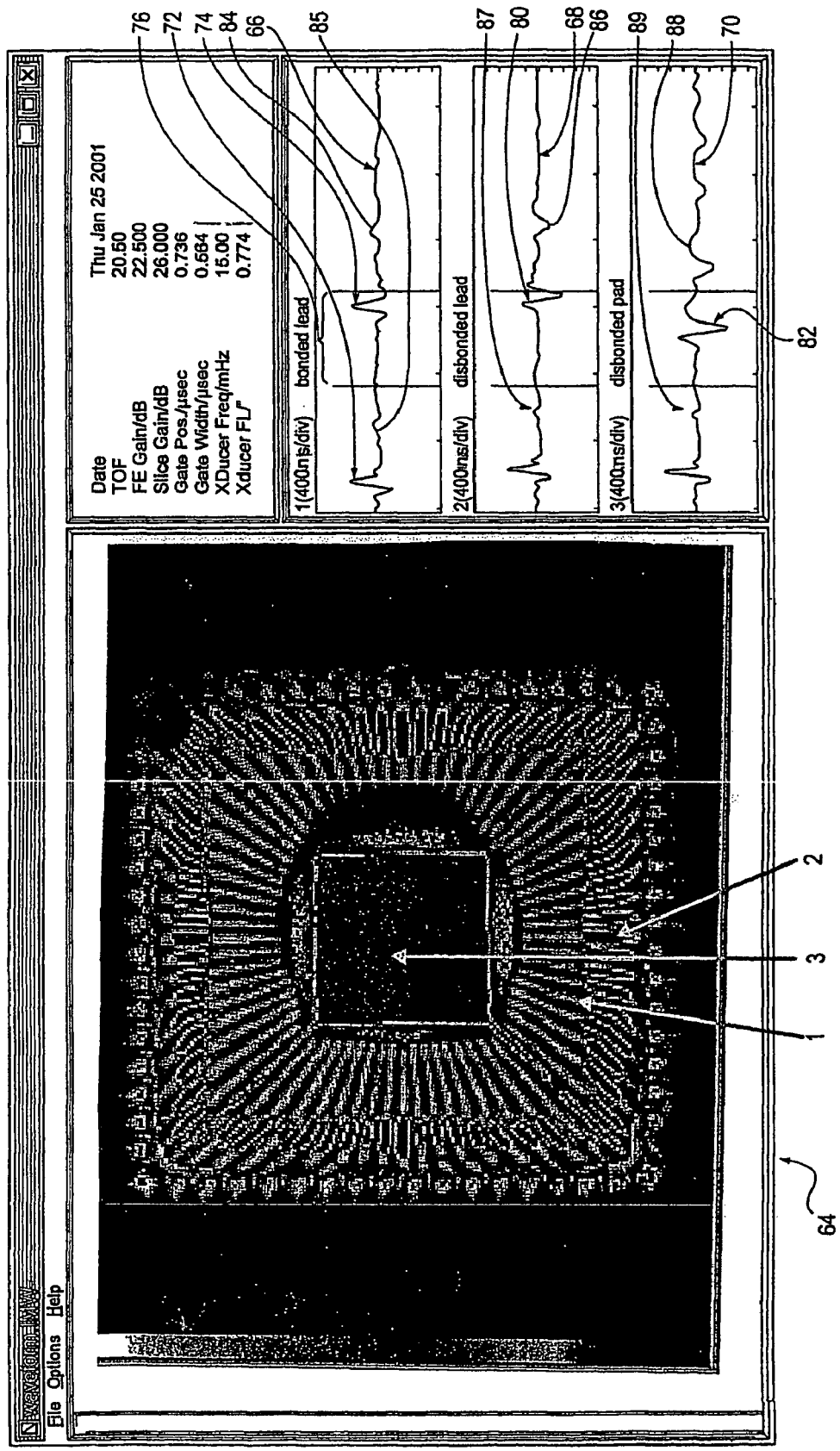
Figure 15:
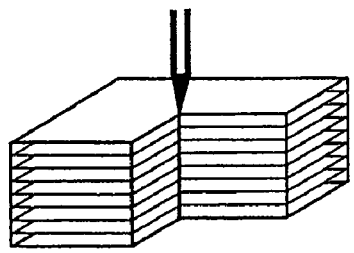

A C-scan (FIGS. 2,2A) results in a capture of peak values of gated reflection waveform segments associated with a collection of data points in an area—specifically the X-Y plane. A C-scan thus results in storage of reflection amplitude values in two spatial dimensions, but does not include time-varying (A-scan type) data. A Q-BAM scan (FIG. 4) is similar to a C-scan, again resulting in a capture of gated peak reflection values for points in an area—specifically the X-Z plane, with no time-varying (A-scan) data being stored. A series of C-scans may be employed (FIG. 15) to capture a 3D set of gated peak reflection values of points in a sample or sample region of interest, again with no time-varying (A-scan) data being stored.

This invention of the copending application Ser. No. 09/911,602 provides a method and apparatus for creating a 4D (three spatial dimensions and one time dimension data set which represents a true virtual sample—one which has all the information stored in memory that could be derived from the real sample, for a given transducer, pulse rate and other operating conditions. As will be explained in more detail below, the data is preferably gathered by repeated interrogations of the sample while varying the focus of the pulsed ultrasonic probe employed such that detectable reflectance features are captured in each of a plurality of stored A-scans. Assuming the transducer depth of field to be less than the sample depth, in certain of the A-scans the reflection features will be stored in in-focus data, and in others in out-of-focus reflection data.

As used in this application, "in-focus acoustic reflectance data" means reflectance data from in-focus impedance features—that is, impedance features which are within the depth of focus of the interrogating ultrasonic probe. "Out-of-focus acoustic reflectance data" means reflectance data from out-of-focus impedance features—that is, impedance features which are not within the depth of focus of the interrogating ultrasonic probe. As used in this application, unless otherwise indicated, "focus" means the location of the interrogating probe.

This 4D data set can be retrieved from memory and manipulated to produce displays of slices of data representing any plane of data: X-Y, X-Z, Y-Z or any diagonal Z plane, with all reproductions exhibiting reflection data from in-focus impedance features in the sample. Three-dimensional volumes may be rotated, dissected and manipulated in any way desired, with all imagery representing in-focus reflection data.

In this application, the direction of the ultrasonic probe shall be taken to be the Z direction or axis. Planes parallel to the Z axis would include the "X-Z" plane, the "Y-Z" plane, or any X-Y diagonal plane or other plane which is parallel to the Z axis, that is, any plane which is not angled with respect to the Z axis. For convenience only, and not by way of limitation, in this application, the "X-Z" plane shall mean all such planes parallel to the Z axis.

In the 3D (spatial dimensions) mode, the invention may be employed to capture space-time data throughout a sample volume or region of interest ("ROI") within a sample volume in any manner or geometry, independent of the scan mode or coordinate system (Cartesian, cylindrical, spherical, etc.).

Figure 16:
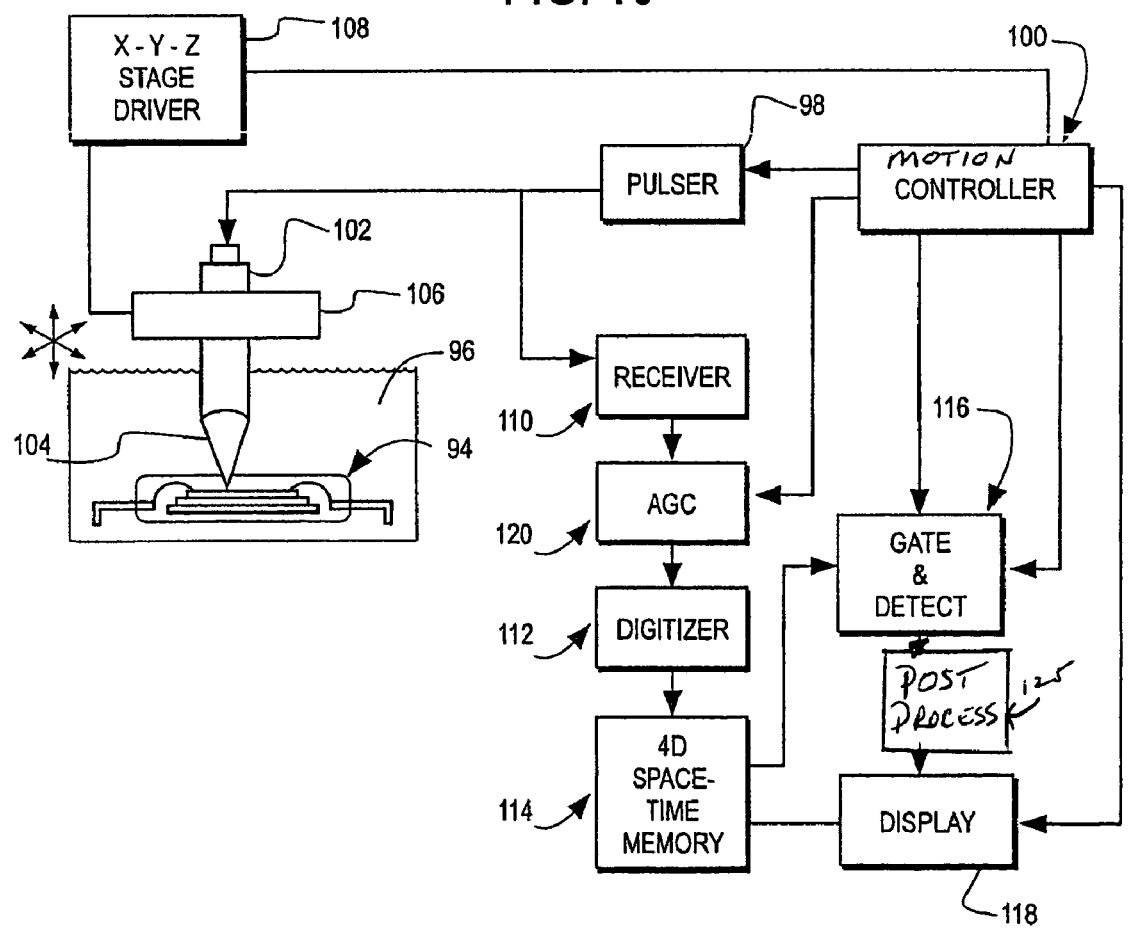
FIG. 16 is a schematic illustration of a preferred form of an acoustic imaging microscope which may be used to practice the teachings of the present invention.

FIG. 16 illustrates in highly schematic form an acoustic imaging microscope implementing the principles of the invention, shown as being adapted to inspect an integrated circuit ("IC") package 94 submerged in a coupling medium 96. A pulser 98, under the control of motion controller 100 excites a transducer 102 to generate a pulsed ultrasonic probe 104, typically at frequencies ranging from 10 MHz or lower to 230 MHz or higher. The transducer 102 is scanned in X, Y, and Z coordinates by an X-Y-Z stage 106 through an X-Y-Z stage driver 108 under the control of motion controller 100. The stage driver 108 and motion controller 100 are constructed in accordance with an important aspect of the present invention and will be described in detail hereinafter.

Acoustic reflections from impedance features in the IC package 96 are sensed by a receiver 110. Acoustic reflectance signals developed by receiver 110 are in analog form. These signals will be described in detail below, here shown as taking the form of acoustic reflectance signals 66, 68, or 70 in FIG. 14, for example. The analog acoustic reflectance signals developed by receiver 110 are supplied to an automatic or computer-driven gain control ("AGC") circuit 120. The AGC circuit 120 is preferably employed to adjust the retrieved acoustic reflectance signal to correct or reduce signal amplitude errors such as may be caused by acoustic energy absorption by the examined sample. The output of the AGC 120 is supplied to a digitizer 112 where the analog signals are quantized, for example by a 2 GHz analog-to-digital converter, into digital bytes for storage in a 4D space-time memory 114.

As will be explained, the 4D space-time memory 114 is of a type adapted to store time-space data corresponding to three spatial dimensions, and associated with each point in 3D space, a set of data corresponding to A-scans associated with each point in space. In accordance with the present invention, for each point in a 3D volume, a sequence of data bytes are stored. The data bytes describe the time-dependent amplitude fluctuations of an acoustic reflectance signal returned upon interrogation of a particular point in sample space. The length of the stored acoustic reflectance signal is a function of the width of a capture gate that is set by the operator or generated by a program or algorithm.

As will become evident from a more detailed description to follow, to create a display the stored space-time data stored within memory 114 is, in one method, gated and peak detected in a gate and detect component 116 which may be a software algorithm or hardware signal processor. A conventional peak-detected output signal from component 116 is processed in a post processor 125. The post processor 125 comprises an aspect of the present invention and will be described at length below.

After being processed in post processor 125, the acquired data signals are employed to modulate a display 120, which may be CRT monitor, for example. Alternatively, as is well known, time-of-flight data may also be displayed. In software, or in a hardware digital signal processor for speed, the system performs a D to A conversion from the 4000 digital values (in our example), then gate and peak detects the desired data to be displayed.

Figure 16A:
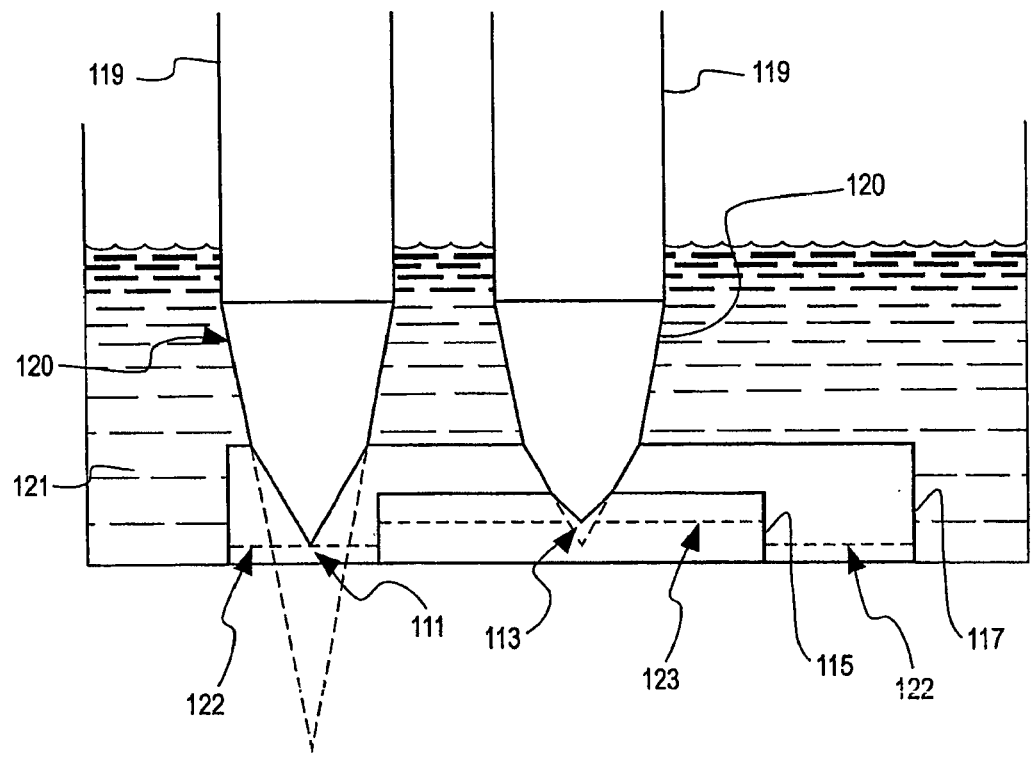

It is of note that in AMI discussions it is customary to speak or write of "scan planes" or "slices", when in fact a scan may not develop a true plane of interrogated points. FIG. 16A illustrates in highly schematic fashion the manner in which, in practice, a scanned plane can, for example, have an offset. An IC package is shown simplified as comprising a silicon die 115 encapsulated by an IC epoxy encapsulant 117. A transducer 119 emits an ultrasonic probe 120 transmitted to the IC package through a couplant such as a body 121 of water. As the acoustic index of epoxy is greater than that of water, the probe focus 111 is displaced toward the transducer 119 and scans a plane 122 within the epoxy encapsulant 117. As the transducer is translated into the region of the die 115, however, the probe focus 113 is displaced closer to the transducer 119 and scans a plane 123 offset from plane 122. For convenience it is common parlance to simply refer to a scan plane. That convention has been followed in this application.

It is a stated object of the invention described and claimed in copending application Ser. No. 09/911,602 to provide means and method for capturing 4D space-time acoustic reflection data in an examined real sample in the form of a "virtual sample" volume or layer. As explained, the virtual sample contains all the data, and permits all the displays, which an operator could have collected during real time examination of live sample. Thus, by this invention, the 4D virtual sample data can be manipulated off-line just as though the live sample were present. Further, as noted, detectable reflectance features are captured in each of a plurality of stored A-scans. Thus, assuming a shallow depth of field of the interrogating transducer compared to the capture-gated sample depth, the stored reflectance data will represent both in-focus acoustic reflectance data and out-of-focus acoustic reflectance data. The reconstructed displays are thus capable of exhibiting in-focus impedance features, out-of-focus impedance features, or combinations of both, or the results of inter-processing data representing both in-focus and out-of-focus impedance features. This capability is not possible with conventional C-Mode scanning acoustic microscopes which capture only peak values of gated signal segments, and discard the remaining information in the A-scan reflection signal from each interrogated x,y,z point within the sample.

Nor is this capability available with a system that makes one X-Y scan across a sample and saves the A-scan waveforms, as the data captured will not represent reflections from in-focus acoustic impedance features throughout the sample volume. Further, systems of this latter type capture only one bulk A-scan reflection for each x,y point in the sample. Simply stated, if 256×240×50 data points are to be inspected (50 being the number of inspection points or levels in the Z dimension parallel to the ultrasonic probe), such a system interrogates only 256×240 points in a single X-Y scan. As it must capture all information in one raster scan, a compromise focus is employed using a high F number transducer lens with a long focal length and therefore large spot size (point spread function). Inevitably, this one-shot approach means that no impedance features are truly in sharp focus, and displays developed from such a dataset will reflect this compromise approach with less-than-optimum resolution.

Let us assume an example where for each of 256×240 x,y points, 50 A-scans will be captured—one for each of the assumed 50 values of "z". If we assume a narrow transducer depth of field compared to the capture-gated depth of the sample or sample region of interest (as is the case in the preferred executions of the invention), only a fraction of the "z" value scans will recover reflectance information from in-focus impedance features. However, that data will permit high resolution image reconstructions, as the impedance features will truly be in sharp focus. Further, the remaining A-waveforms from remaining z-differentiated x,y points may also contain very valuable data. By processing the in-focus reflection data with out-of-focus reflection data, significant additional information about internal reflection features can be gleaned.

It is highly desired in the inspection of a sample such as an IC package to gather as much information as possible about any internal voids, disbonds, cracks, occlusions, interfaces and other acoustic impedance features. Acoustic reflections from internal impedance features carry a tremendous amount of information in the detected A-scan waveforms. Every undulation in the return waveform indicates an acoustic impedance mismatch of some character within the examined sample.

There are many factors which can influence the amplitude of the A-scan signal associated with each interrogated point in a sample, including:

a) the location in the sample of the transducer focus;
b) the size of the impedance feature (which influences the percentage of the acoustic wave which is intercepted);
c) the shape of the feature (concave, flat, convex, irregular, e.g.) and its orientation which will influence the direction of wave reflection or refraction;
d) the scattering property of the feature (how rough or smooth the feature is relative to the acoustic wavelength);
e) the acoustic impedance of the feature;
f) the impedance mismatch between adjacent features;
g) the absorption properties of the various materials through which the ultrasound probe and return signal passes;
h) the thickness of the sample materials encountered and the total depth of the sample;
i) the spot size (point spread function) and location of the ultrasonic probe;
j) acoustic energy conversion between acoustic wave types (compression, surface, shear);
k) reverberation between interfaces and other impedance features;
l) interference cancellation effects;
m) the frequency of the ultrasound employed (which dramatically impacts acoustic absorption);
n) masking effects (anomalies close to interfaces may mask closely adjacent features, as described);
o) focus errors due to refraction;
p) the height or energy of the pulses which are employed to excite the transducer;
q) trailing shear wave effects;
r) sample edge effects;
s) depth of field of the transducer;
t) number of features encountered (each reduces acoustic energy);
u) noise (mechanical, electrical or thermal);
v) features in the unfocused part of the beam bundle;
w) transducer ringing;
x) shadowing; and
y) specimen material anisotropy.

It is obviously critical therefore that as much internal acoustic impedance data as possible be gathered from the sample, and that such data be stored for later signal processing, analysis, interpretation and display.

A method of the invention described in copending application Ser. No. 09/911,602 (hereinafter referred to as the '602 application) is directed to capturing 4D space-time acoustic reflectance data to create a virtual sample volume or spaced virtual sample layers which characterize impedance features in a sample volume interrogated with a pulsed ultrasonic probe. The method comprises, in one execution, employing a pulsed ultrasonic microscope probe to interrogate a sample at three-dimensionally varied locations in the sample. Data produced by the pulsed microscope probe are developed. The data include for each location interrogated a digitized A-scan for that location. Finally, the developed data are stored in a data memory. In another aspect the '602 application method involves: a) deriving and storing a digitized non-peak-detected time-varying reflection signal for each location in a series of locations in a first plane of the sample volume; and b) deriving and storing a digitized non-peak-detected acoustic signal for each location in a series of locations in a second plane of the sample volume, said second plane being displaced from said first plane. The planes may be adjacent or spaced. The first plane may be the X-Y plane, or alternatively it could be the X-Z plane, Y-Z plane, or another plane containing the Z axis.

The stored signals create a 4D virtual sample data store containing data representing for each point in an interrogated sample volume three spatial dimensions and a time variable. The time variable comprises a digitized time-varying waveform characterizing reflections from acoustic impedance features in the examined sample.

The preferred apparatus for capturing data in accordance with '602 application invention is an X-Y-Z raster scanning acoustic microscope as illustrated in FIG. 16 and described above. In the context of data capture employing a scanning acoustic microscope having a pulsed ultrasonic probe as depicted in FIG. 16, the method of the present invention is directed to capturing 4D space-time virtual sample data characterizing acoustic impedance features in an examined volume of a sample interrogated with the pulsed ultrasonic probe. The method involves: a) raster scanning a first plane in the sample; b) storing a digitized, non-peak-detected, time-varying acoustic reflectance signal for each interrogated point in the plane; c) raster scanning a second plane in the sample; d) storing a digitized, non-peak-detected, time-varying acoustic reflectance signal for each interrogated point in the second plane; and e) repeating the raster scanning and storing operations to capture space-time data representing a virtual sample volume corresponding to the examined real sample volume or region of interest.

The method of the '602 application preferably includes controlling the focus of the probe during each scanning operation such that each of the interrogated planes are within the depth of field of the probe-developing transducer when scanned. The scans may be made of variably spaced planes concentrated, for example, in a particular region of interest ("ROI") in the sample predicted to contain impedance features desired to be examined thoroughly. Or, more often, the method of the '602 application will be employed to successively scan adjacent planes. The planes may be X-Y or X-Z planes, or other planes containing the Z axis. However, most commonly the successively scanned planes will be those displaced in the Z axis of the probe. In the latter case, the displacement of the scans ideally is caused to be substantially equal to the depth of field of the transducer.

Figure 17:
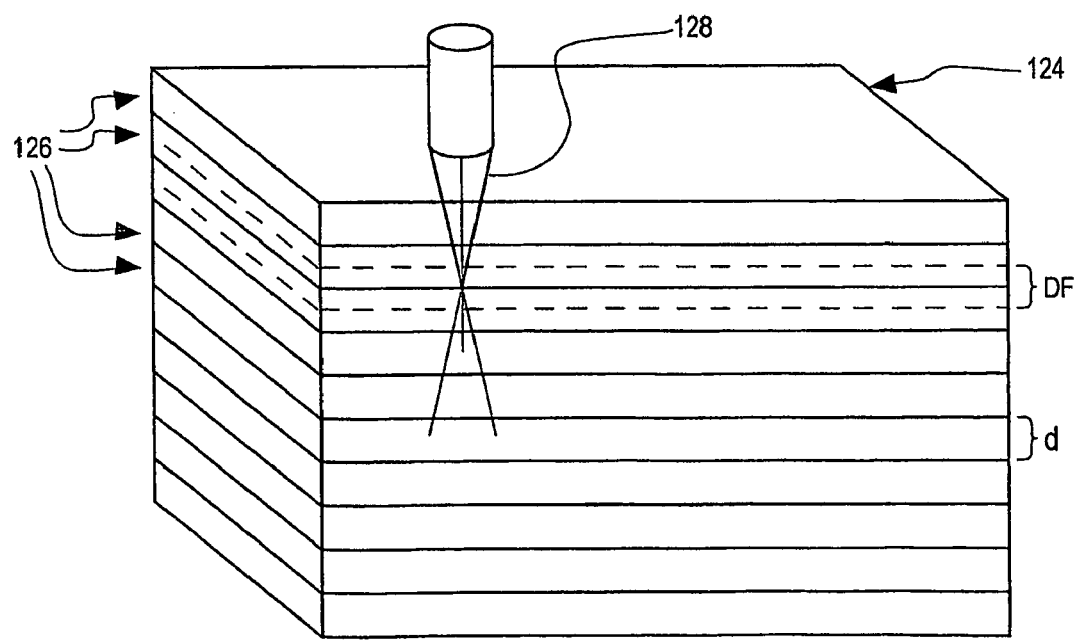
FIGS. 17–20 are schematic diagrams depicting the practice of various aspects of 4D data capture employed in certain applications of the present invention.

FIG. 17 illustrates the last-described condition wherein a sample 124 is scanned in successive planes 126 displaced in the Z direction a distance "d" equal to the depth of field "DF" of the transducer 128. In this condition reflectance features are captured in stored in-focus acoustic reflectance data, and in stored out-of-focus acoustic reflectance data. As explained, all impedance features will be captured in reflection data from an "in focus" condition, that is, a condition wherein the features are within the depth of field of the transducer employed to generate the ultrasonic probe.

Figure 18:
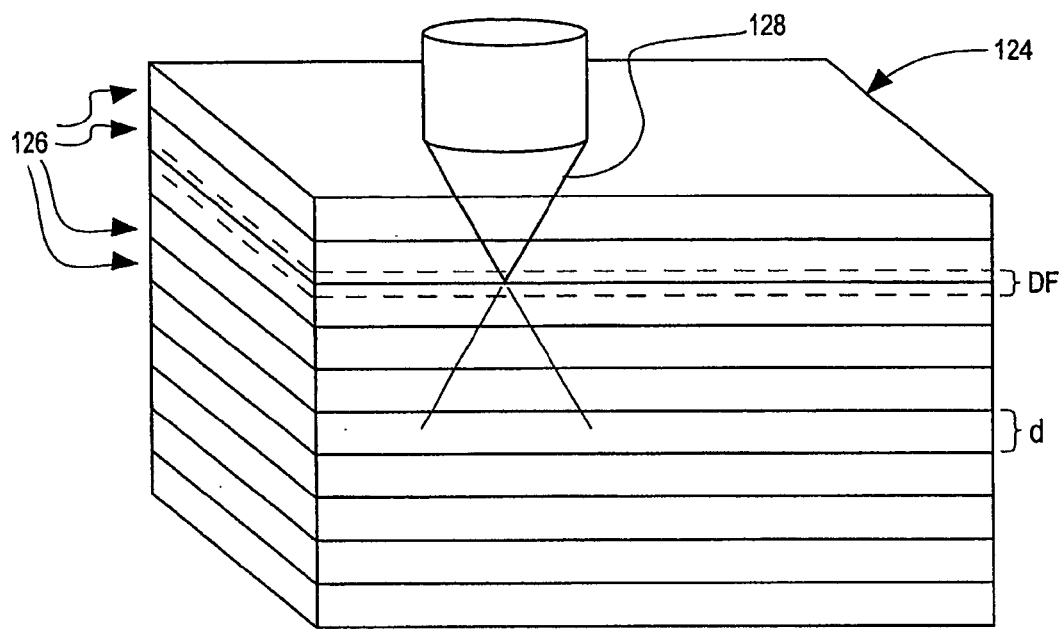

In certain applications or parts of the sample where data reduction is deemed more important than data density and display fidelity, the scans may be made in successive planes displaced in the direction of the probe by a distance which is greater than the depth of field of the transducer, creating an underscan condition. This condition is illustrated in FIG. 18 wherein like reference numerals have like meaning to those in FIG. 17.

Figure 19:
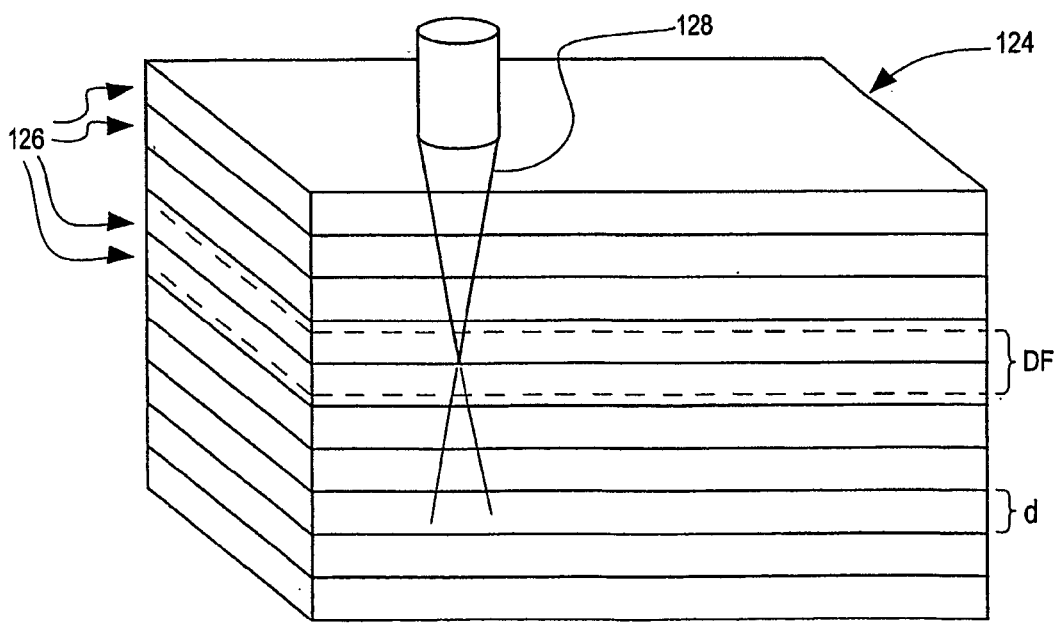

And finally, in applications where maximum information capture is of greater concern than data capture speed or data storage requirements, the scans may be made in adjacent planes displaced in the direction of the probe by a distance "d" which is less than the depth of field of the transducer 128, creating an overscan condition. See FIG. 19 wherein reference numerals have like meaning to those in FIGS. 17 and 18.

Figure 20:
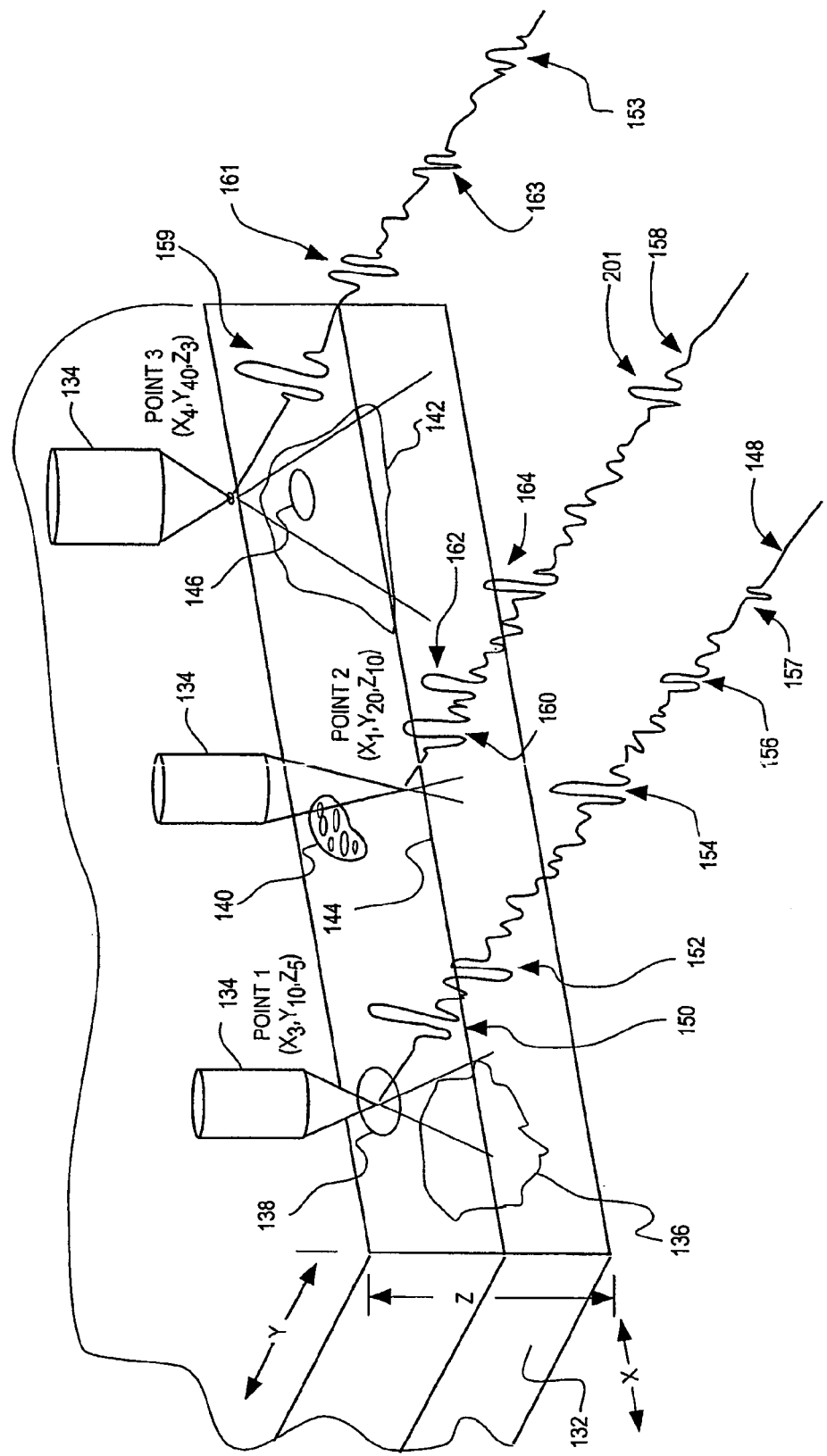

FIG. 20 illustrates a sample 132 which has been interrogated by an X-Y-Z raster scan or other scan mode to capture 4D space-time data in accordance with the method of the '602 application. For simplicity of description, FIG. 20 shows hypothetical A-scan waveforms developed from ultrasonic probe interrogations at three locations within the sample designated (x3,y10,z5), (x1,y20,z10) and (x4,y40, z3), hereinafter termed points 1, 2, and 3, respectively. The sample is shown as having impedance features in the forms of a crack 136, a large air bubble 138, a large occlusion 140, a disbond (air gap) 142 at an interface 144, and a small air bubble 146.

The acoustic reflectance signal (A-scan) 148 from point 1 exhibits a strong front surface reflection 150, a strong inverted phase reflection 152 from air bubble 138, a positive reflection 154 from interface 144, a weak positive reflection 156 from crack 136, and a very weak inverted phase reflection 157 from the back surface of the sample.

The A-scan 158 from Point 2 exhibits a positive front surface reflection 160, a strong closely adjacent positive reflection 162 from occlusion 140, a strong positive reflection 164 from the interface 144, and a weak reflection 201 from the back surface of the sample.

In practice, the reflections 152 and 162 will likely be partially masked by the strong front surface reflections 150, 160.

A-scan 153 shows a strong reflection 159 from the sample front surface, a weak inverted phase reflection 161 from the small air bubble 146, and a strong reflection 163 of inverted phase from the disbond 142. The A-scan 153 exhibits no reflection from the back surface because of the total shadowing of the back surface by the disbond 142.

As shown in FIG. 20, in accordance with a preferred execution of the '602 application invention, the ultrasonic probe is focused at Points 1, 2, and 3 in order to assure that the impedance features at those locations will be captured in in-focus reflectance data, as defined herein.

As explained above, the data is preferably gathered by repeated interrogations of the sample while varying the focus of the pulsed ultrasonic probe employed such that detectable reflectance features are captured in each of a plurality of stored A-scans. Assuming the transducer depth of field to be less than the sample depth, in certain of the A-scans the reflection features will be stored in in-focus reflection data, and in others in out-of-focus data.

Referring to FIG. 20, if it were desired to display data at level z5, for example, retrieved from a 4D memory such as shown at 114 in FIG. 16, in A-scan 148 inverted reflection 152 from air bubble 138 would represent in-focus reflectance data, that is, data from an impedance feature (air bubble 138) that was within the depth of field of the transducer 134 when interrogated. However, reflections 154, 156, and 157 from interface 154, crack 156, and the back surface, respectively, would represent out-of-focus data—that is, data from out-of-focus impedance features (impedance features which were not within the depth of focus of the transducer 134).

Taking another example, in A-scan 158 reflectance data from occlusion 140 (reflectance 162) represents out-of-focus data, as the transducer 134 was focused on interface 144 when A-scan 158 was developed. However, in contrast with A-scan 148, in A-scan 158 interface 144 is within the depth of field of the transducer 134 and reflection 164 from interface 144 is in focus. Or stated another way, the interface 144 is an in-focus impedance feature in A-scan 158.

As noted, there are applications where it will be of value to create an image of a feature by gating the A-scan at an out-of-focus impedance feature. For example, in a sample which has a well-bonded silicon-to-silicon interface, the imaging of an absorptive or scattering feature at the interface will be difficult because of the close impedance match at the interface. A completely well-bonded sample interface gives a null result. A technique called "loss of back echo" is commonly used in this situation. This technique focuses the ultrasonic probe approximately at the interface of interest, and gates at the back surface of the sample. By scanning along the interface and observing (gating) for a loss of echo from the back surface, an in-focus image of such a feature can be created.

Each of the A-scans 148, 158, 166 exhibits many small undulations which contain valuable information about the impedance features within the sample. By the '602 application invention, not only are the major echoes captured, but all information in the A-scan at each interrogated point throughout the volume of the sample are also stored. Using a sampling rate of 1 GHz, for example and an A-scan capture gate of 4 microseconds, 4000 data samples will be captured and stored in memory.

The amount of data that will be stored is the product of the scanning resolution in the X, Y plane, the number of planes scanned along the Z axes, and the number of data samples developed per A-scan (4000 in the present example). By way of example, the X-Y scanning resolution might be set at 256×240, 10 planes may be scanned in the direction, and 4000 data samples may be stored per A-scan.

In accordance with an aspect of the present method, as alluded to above the captured A-scan data are amplified before digitization and storage. The amplification is adjusted to compensate the stored data (and ultimately data displays) for acoustic reflectance signal amplitude errors. One source of significant signal amplitude errors which may be compensated for is absorption of acoustic energy by the sample. All samples absorb acoustic energy, and as is well known, some materials such as IC epoxy encapsulant are very highly absorptive of acoustic energy, with the result that reflections from impedance features at the bottom of the sample will appear weakly reflected simply because the two-way transmission of the acoustic waves to and from such a feature will result in dramatically more absorption than from a feature near the surface.

Unlike the described prior method which makes a single scan in the X-Y plane and stores the A-scans of each x,y point in that plane, in the method of the '602 application, multiple acoustic reflectance signals for each x,y plane interrogated may be retrieved and individually viewed. Or they may be retrieved and processed together to develop new acoustic reflectance information not otherwise obtainable. Processing together signals representing data characterizing reflections from "out-of-focus" impedance features and "in-focus" features is apt to produce valuable new insights as to the nature of the examined features.

When composite acoustic reflectance signals thus formed are employed to modulate a display of examined volume data, for any displayed slice at any set value of "x", "y", or "z", all parts of the display will exhibit acoustic reflectance information from in-focus impedance features.

The complete 4D space-time dataset captured by the method and apparatus of the present invention represents a virtual sample for the given transducer. Any type of image that is desired can be generated from this data. All of the resulting images will be uniformly in focus and of optimum brightness. All possible data for the sample for a given transducer will have been captured.

For attenuating samples, the ability to adjust for image brightness for each of many Z positions is valuable. Even when the entire thickness of a sample is within the focal region of the transducer, the brightness of a shallow feature may be significantly higher than the brightness of a deep defect if the gain is not adjusted. Even amounts of attenuation that are greater than the dynamic range of the waveform digitizer can be compensated for.

In accordance with the '602 application invention, compared to prior methods, reflectance features are captured with dramatically greater detail. In the present example, the 10 A-scans will be very different in amplitude configuration. The amplitude value characterizing a particular impedance feature will vary significantly among the 10 A-scans depending principally upon the location of the transducer focal point relative to the location of the particular impedance feature.

For example, if the transducer is positioned in the X-Y plane at x10y30 and excited 10 times at different values of "z" throughout the depth of a sample, 10 A-scans will be developed. A detectable impedance feature located at x10y30z5 will appear in each A-scan, but at different amplitudes, depending, as stated, upon the location of the interrogating probe relative to x10y30z5.

In certain A-scans the particular impedance feature will be in focus, as defined herein, and in others it will be out of focus. In accordance with one execution of the '602 application invention all 4000 sampled values for each of the 10 (in this example) A-scans will be stored.

In preferred executions of the '602 application invention, the four axes in the 4D data are: 1) X position of transducer (encoder counts)—measured in scanner space;
2) Y position of transducer (encoder counts)—measured in scanner space;
3) Z position of transducer—measured by TOF value ($\mu$sec; and
4) Time axis of A-scan—time between points governed by sampling rate (nsec or $\mu$sec)

The following examples will assist in an understanding of the '602 application invention. Assume ten scans at different values of the Z position of the transducer (slices). Assume an image resolution of 256 (X) and 240 (Y). Further assume that the 'capture gate' always starts before the top surface of the sample and the duration of the 'capture gate' is long enough to include a little more than the entire thickness of the sample. Finally, assume that there are 4000 points in each A-scan.

EXAMPLE 1

For one unique set of points in 4-space, which correlates to a unique position of the transducer (X1, Y1, Z1), there will be the 4000 values, one for each of the A-scan points captured at that position. If the capture gate is set as indicated for this sample, then there will be A-scan values that are equally spaced in time and that start before the top surface of the sample and that end after the bottom surface of the sample.

EXAMPLE 2

For another unique set of points in 4-space (X3, Y4, and T='150 samples later than the sample point that correlates to the sample surface',) there will be 10 different values, one for each of the 10 different Z positions of the transducer used for the ten different slices.

EXAMPLE 3

For a third unique set of points in 4-space (Y19, Z6, and T='112 samples later than the sample point that correlates to the sample surface',) there will be 256 different values, one for each of the 256 different X positions of the transducer at which data were captured.

The resulting virtual sample will thus be captured in a full 4D data set which can be processed and displayed as though the live sample were present. Having the virtual sample may in some respects be an advantage over operations in real time, as processing speeds need not be so rapid when analyzing a virtual sample off line.

AMI Scanning of Non-Rectangularly Bounded 2D and 3D Space

Figure 1:
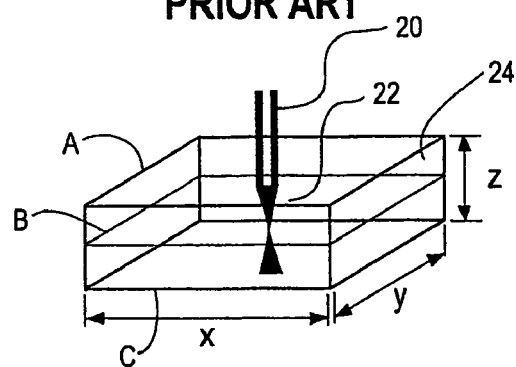
FIGS. 1–13 and 15 illustrate in highly schematic fashion various prior art AMI scanning modes.
Figure 1A:
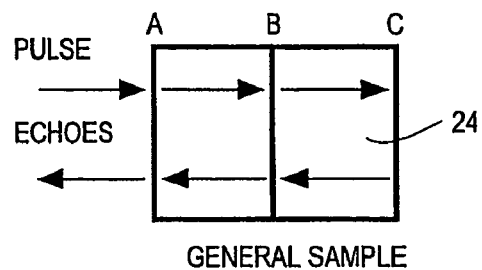
FIGS. 1A, 1B, 2A and 14 are illustrations useful in understanding general AMI principles.
Figure 1B:
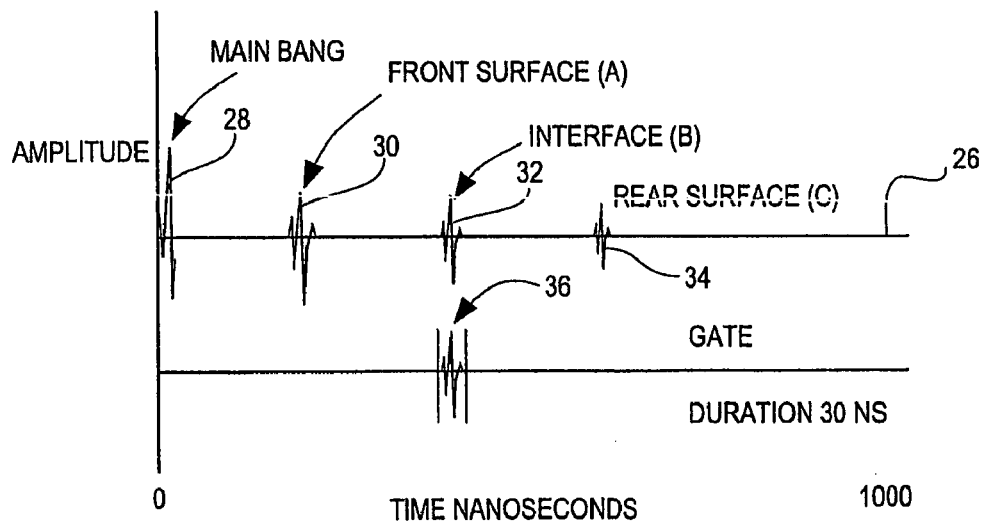

For purposes of the present application the following definitions shall apply:

1) "Rectangular area" or "2D rectangular space" or "2D rectangularly bounded area" (or space) means a two dimensional area or space having right angle corners, as shown in FIG. 1, for example.
2) "Rectangular volume or region" or "3D rectangular space" or "3D rectangularly bounded space" means a three dimensional volume, region or space with all sides meeting at right angles, as shown in FIG. 17, for example.
3) "Space" means either a two dimensional area or a three dimensional volume.
4) "Non-rectangular area" or "2D non-rectangular space" or "2D non-rectangularly bounded area" (or space) means any two dimensional area or space other than one having right angle corners.
5) "Non-rectangular volume or region" or "3D non-rectangular space" or "3D non-rectangularly bounded space" means a three dimensional volume, region or space in which at least one pair of sides meet at an angle which is not 90 degrees.
6) "Irregular area" or "2D irregular space" or "2D irregularly bounded area" (or space) means any non-rectangular two dimensional area or space in which at least one boundary is curved.
7) "Irregular volume or region" or "3D irregular space" or "3D irregularly bounded space" means a non-rectangular three dimensional volume, region or space having a curved surface.
8) "Raster scan" means a scan of a space with a series of spaced parallel scans.
9) "Rectangular raster scan" means a raster scan of a space in which the scan trace envelope is a rectangle.
10) "Non-rectangular raster scan" means a raster scan in which the scan trace envelope is other than a rectangle.

One aspect of the present invention concerns an improved method and apparatus for use in scanned acoustic micro imaging comprising driving an acoustic probe with a multi-axis motion controller having inputs to its axes effective to cause said probe to interrogate a predetermined non-rectangularly bounded 2D or 3D space within the sample.

Figure 15A:
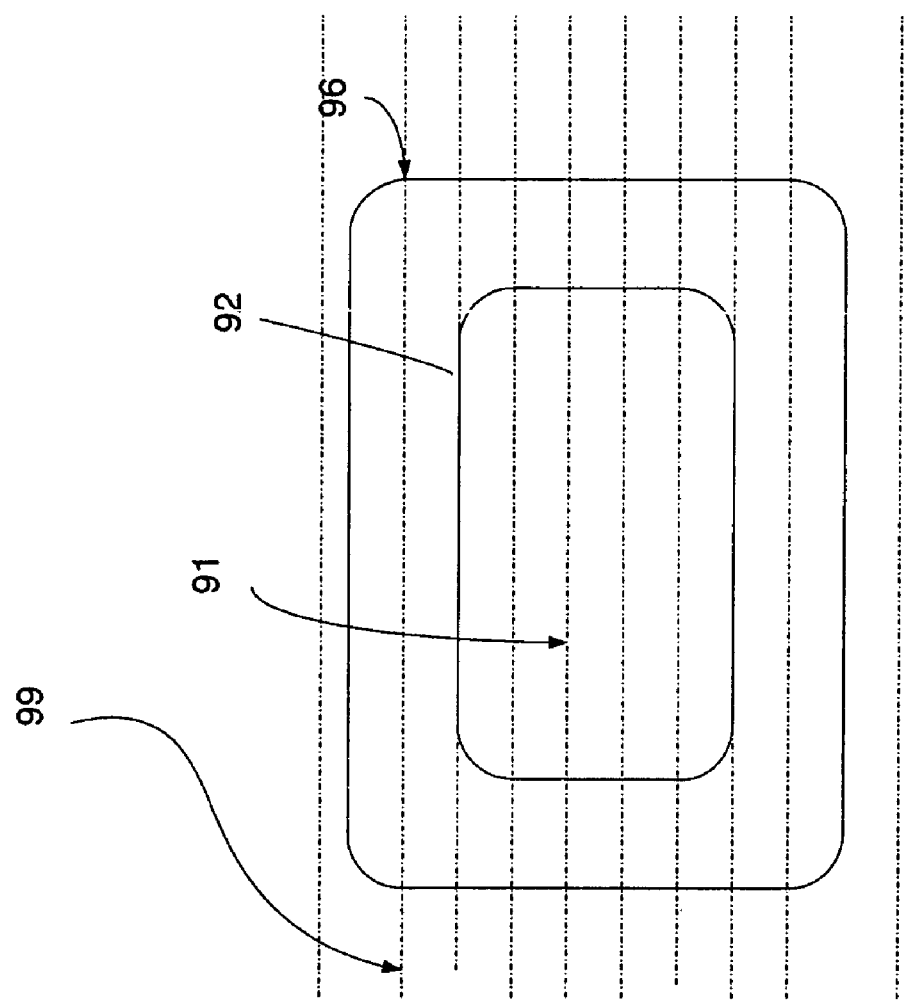
FIGS. 15A and 15B depict diagrammatically the manner in which non-rectangularly bounded contours and other areas are scanned conventionally.

As discussed in connection with FIGS. 15A and 15B, scanning of a 2D or 3D non-rectangularly bounded space using conventional rectangular rasters is slow and inefficient. In accordance with an important aspect of the present invention, 2D or 3D spaces with contoured or other non-rectangular boundaries are scanned with more efficient processes.

Figure 15B:
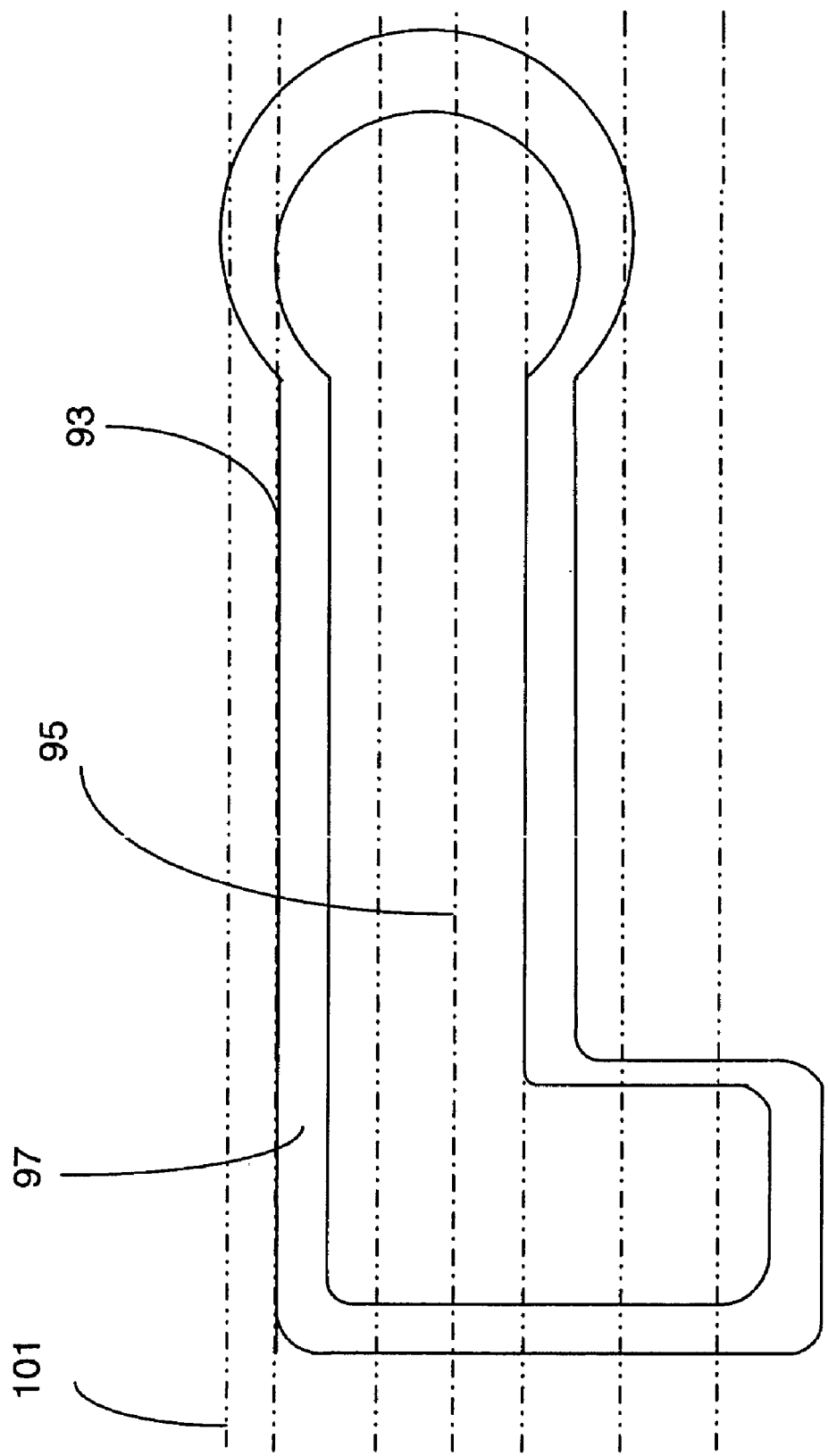

FIG. 21 illustrates a medical package 170 like that shown in FIG. 15B, being contour scanned according to the principles of the invention. Using novel AMI stage motion control, as will be described, probe 104 is caused to trace the irregular configuration of the seal area 172. It may be desired to inspect not just a line, but a strip along the contour of the package, in which case the probe would be caused to trace a series of contour scans which are geometrically similar, but of slightly different scale, as shown at 174, 176 in FIG. 21A (an enlarged portion of the seal area shown in FIG. 21). The series of contour scans may be accomplished by inserting offset commands into the probe motion controller (100 in FIG. 16).

A non-rectangularly bounded contour scan as shown can be extended to three dimensions, while preserving focus, by making an adjustment in the probe depth and repeating the process. Alternatively, contours of like scale at various selected probe depths can be run in sequence, followed by similar scans at successively different scales.

Figure 22:
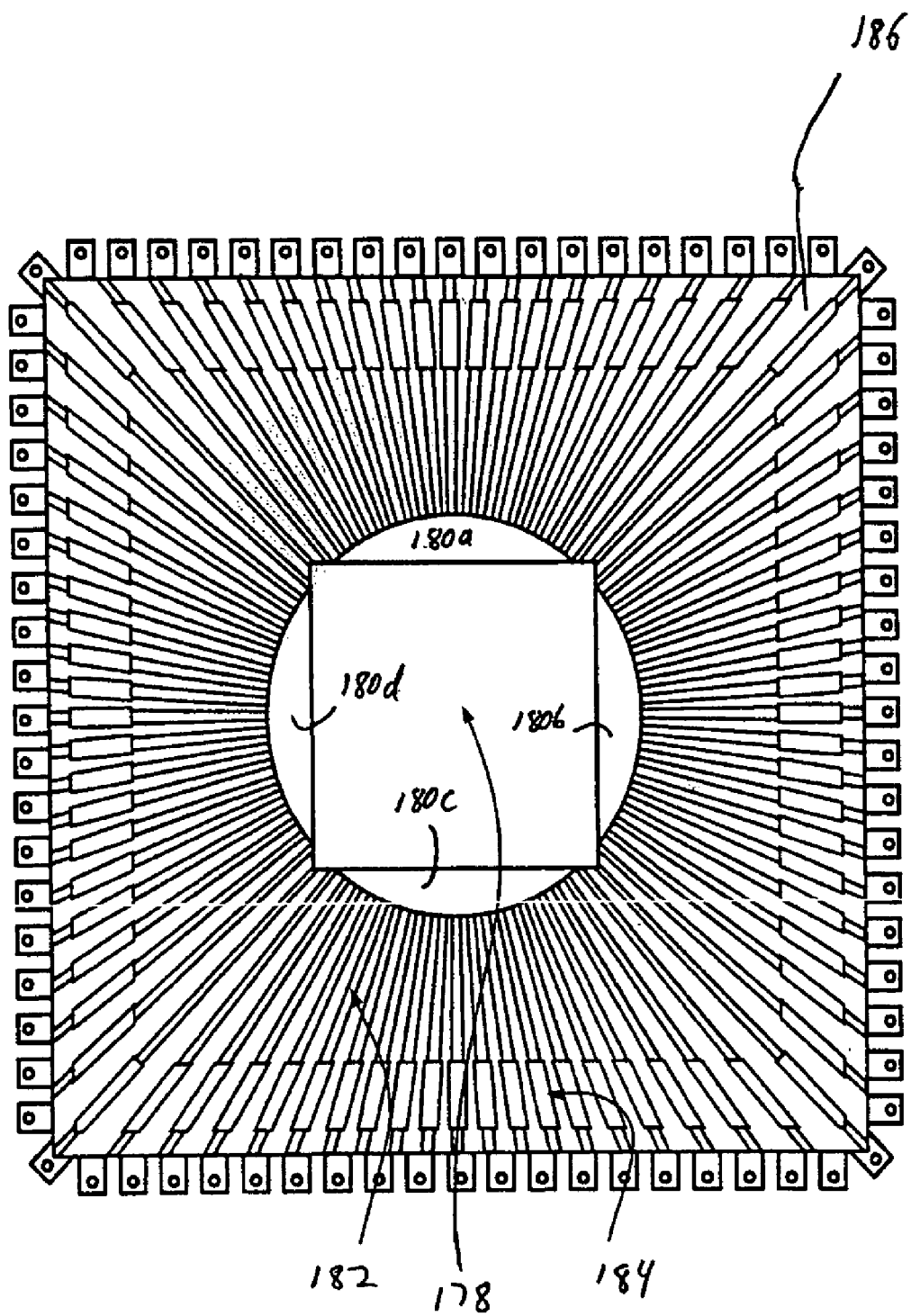

FIG. 22 depicts a semiconductor chip package comprising an IC die 178 bonded to a bonding pad, elements of which are shown at 180a, 180b, 180c, and 180d, from which extends radial leads 182. The leads 182 are bonded in a circumferential array of bond 184. As the lead bonds 184 are often an area where defects occur, it would be useful in certain applications to program the motion controller (more on that subject below) to cause the probe to contour scan in 2D or 3D the circumferential track 186 embracing the array of lead bonds 184.

It may also be desirable to acoustically inspect one or more of the die bond pad elements 180a, 180b, 180c, and 180d. FIG. 22a illustrates how an non-rectangularly bounded space such as bonding pad element 180a, may be inspected by causing the acoustic probe to sweep over the pad element 180a in what is herein termed a non-rectangularly, or irregularly, bounded space. Alternatively, the same pad element 180a may be scanned in a contour mode progressively by reducing the scan radius, as shown diagrammatically in FIG. 22B. As will become evident from the ensuing description, any non-rectangular probe scan of an area, such as represented by pad element 108a, or an area or volume of any arbitrary dimensions, can be inspected using the principles of the present invention.

Figure 23:
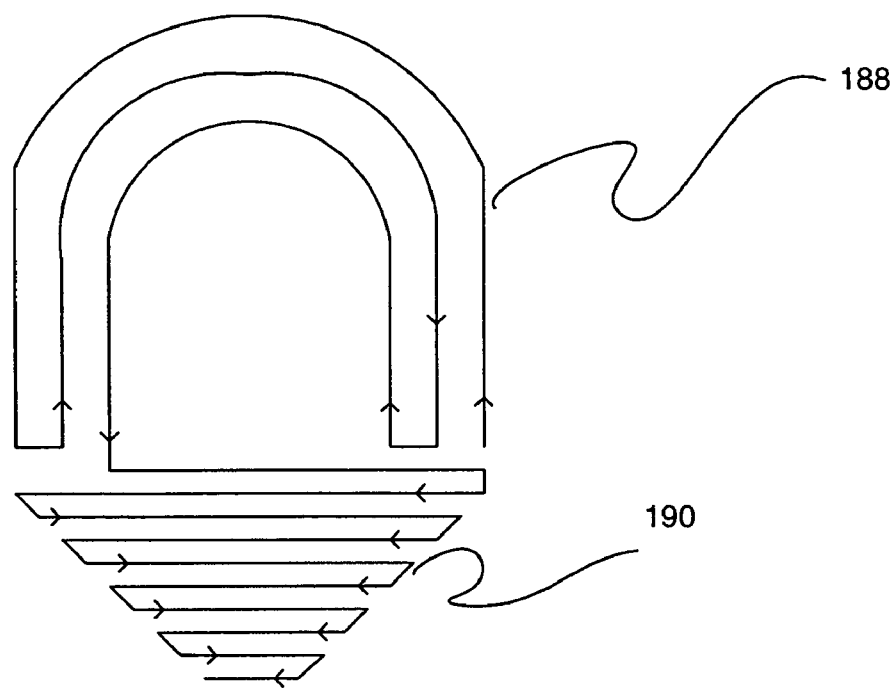
Figure 24:
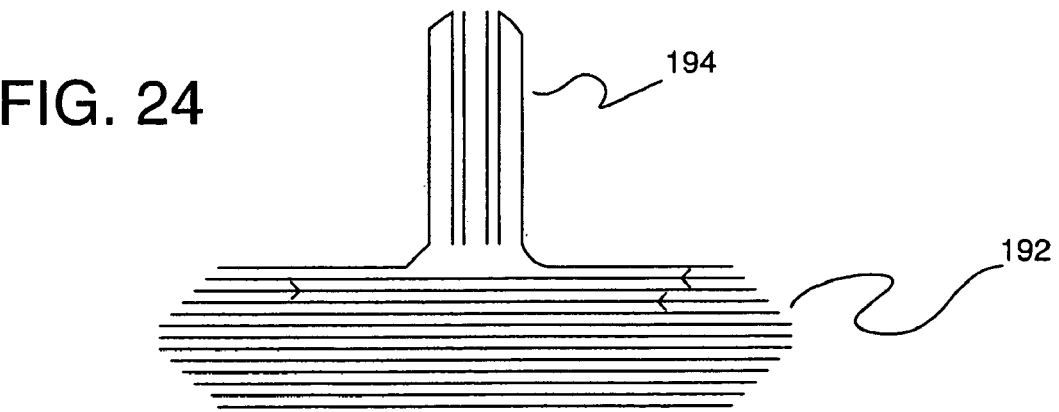

FIG. 23 illustrates a hybrid scan mode according to the invention wherein a contour scan is employed to scan what be characterized as the handle 188 of a basket, and a raster scan is employed to scan the body 190 of the basket. In FIG. 24, a raster scan in one direction is performed on the base section 192 of an irregularly bounded area and a raster scan at a different direction is performed on an upright section 194 of the area.

Figure 24A:
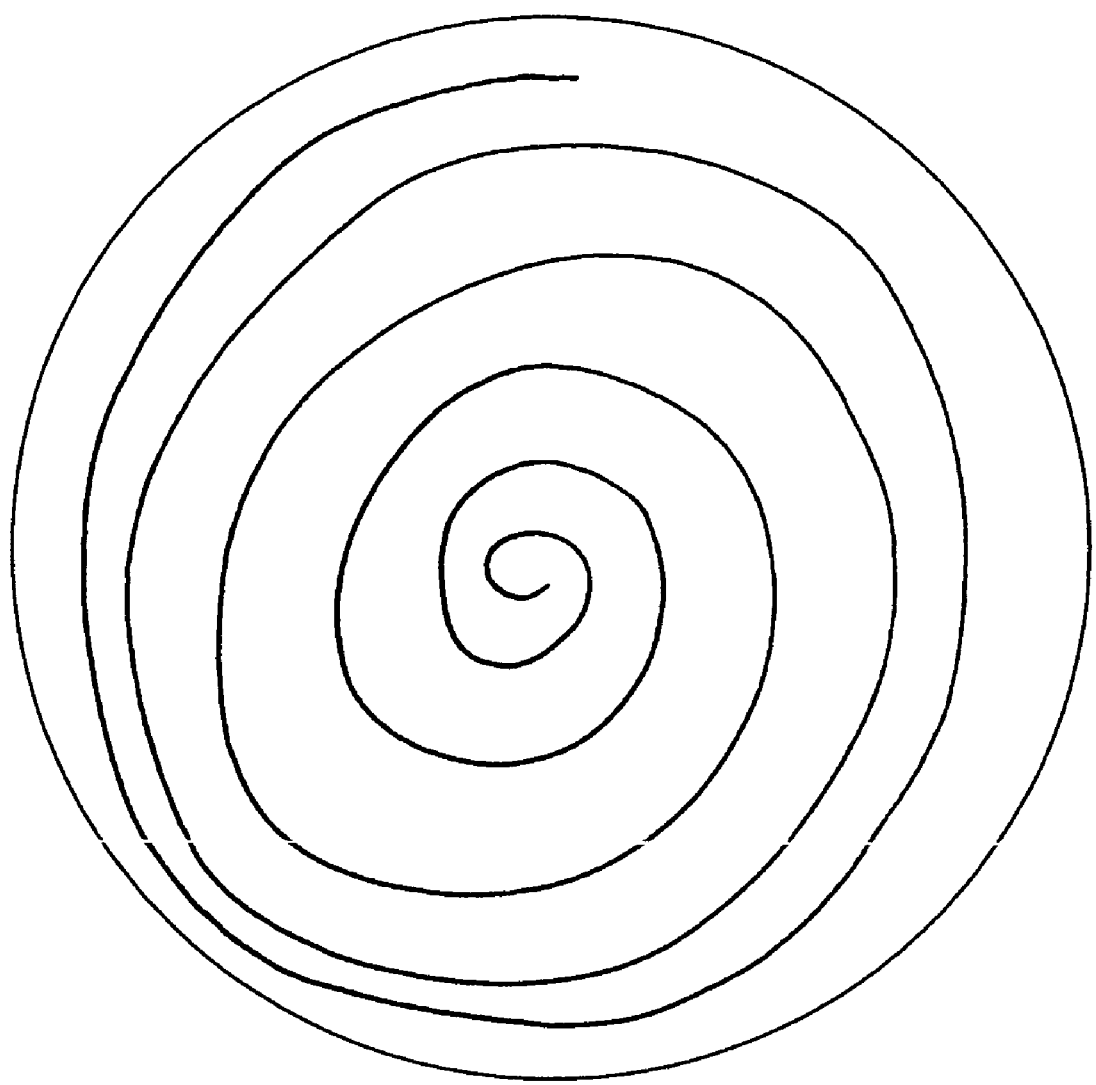
Figure 24B:
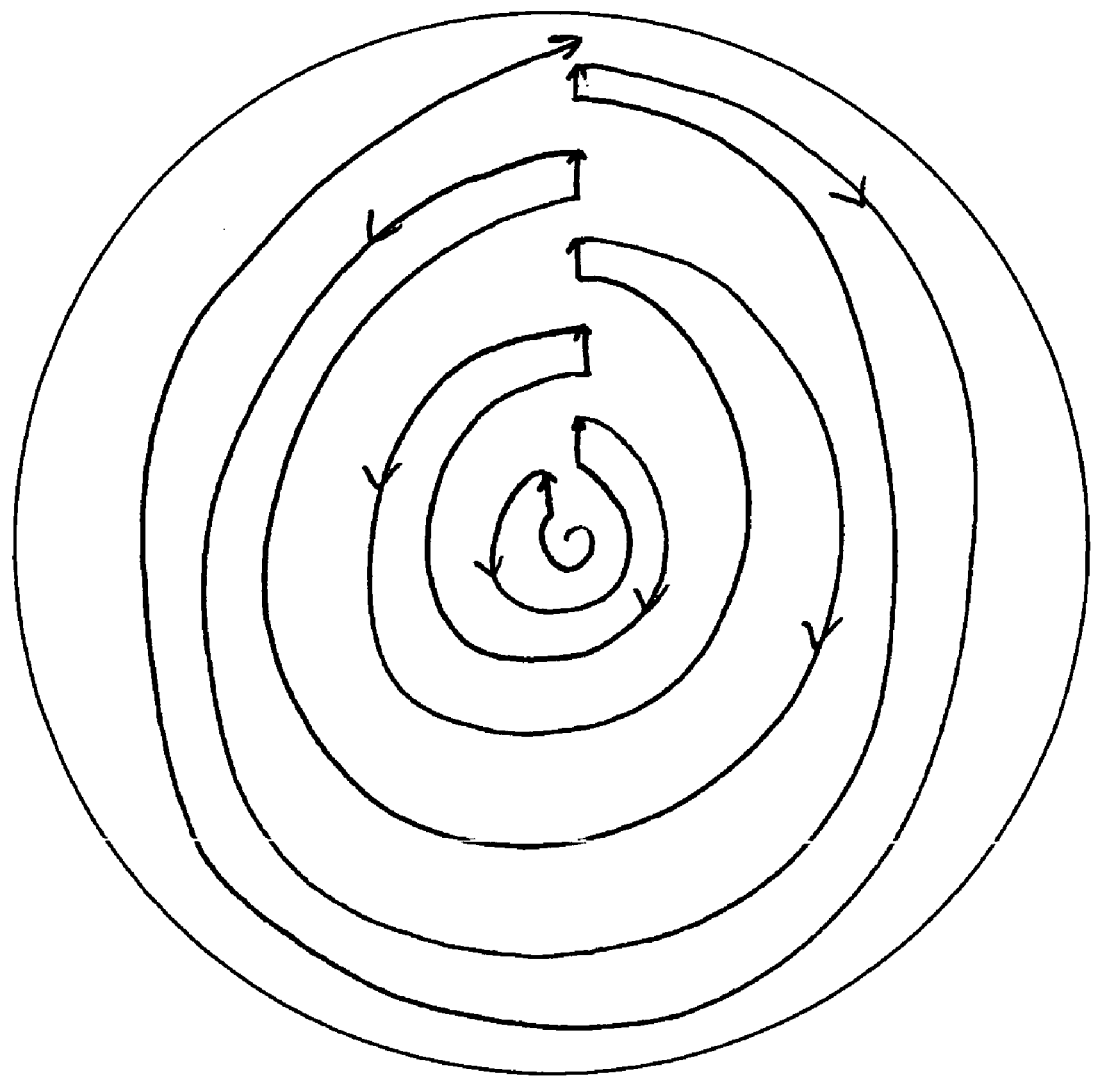

FIGS. 24A and 24B illustrate two methods according to the present invention for quickly and efficiently scanning a circular sample such as a semiconductor wafer. In FIG. 24A, a spiral scan of the acoustic probe is accomplished by appropriate commands from the motion controller to the XYZ stage. For higher speed scanning, the sample may be rotated as the probe is driven along a radius of the sample. For a uniform data acquisition rate, in applications where that is desirable, the rotational velocity of the sample is appropriately decreased in relation to the distance of the probe from the sample center.

FIG. 24B illustrates a second approach wherein the probe is driven to trace concentric contours across the sample. Again, as in FIG. 24A, for a uniform data acquisition rate the rotational velocity of the sample is appropriately decreased in relation to the distance of the probe from the sample center.

Figure 25:
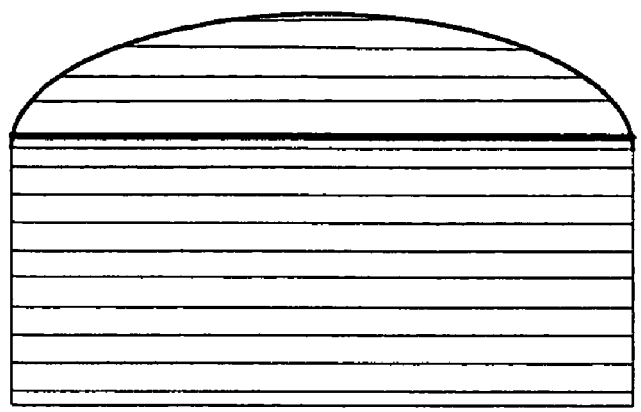

Additional examples of the unlimited number of possible executions of AMI inspection three dimensional traces which may be made according to the invention are illustrated in FIGS. 25–29. FIG. 25 shows a layer by layer inspection, using a raster mode, of a truncated circle such as represented by the die bond pad element 180a. By stepping the probe along an axis perpendicular to the raster plane, the entire volume can be inspected in focus.

Figure 26:
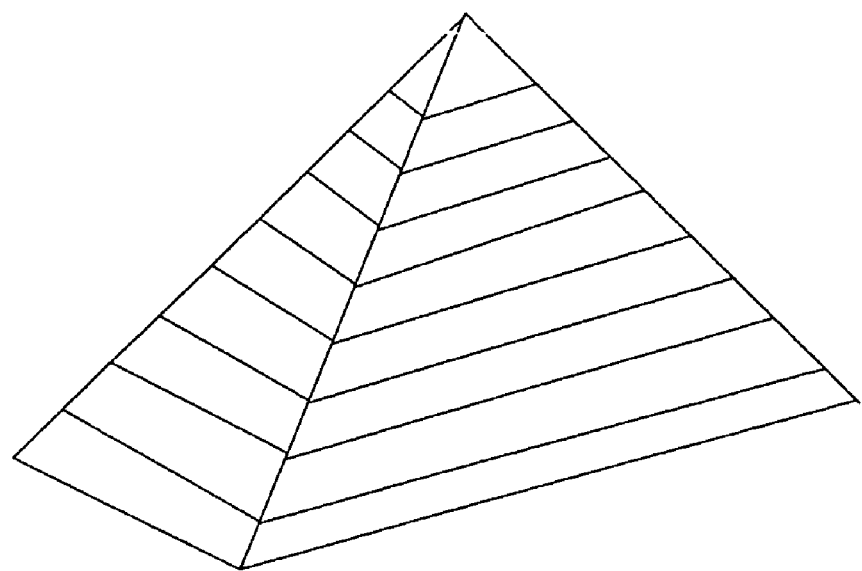
Figure 27:
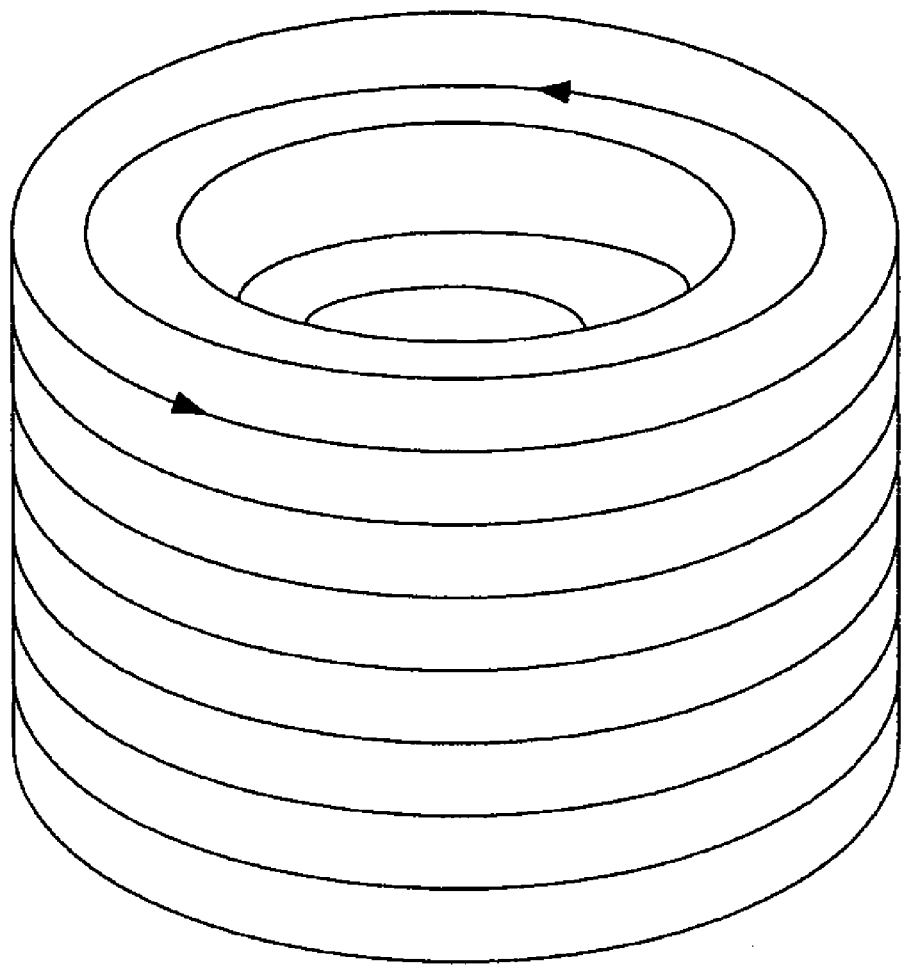
Figure 28:
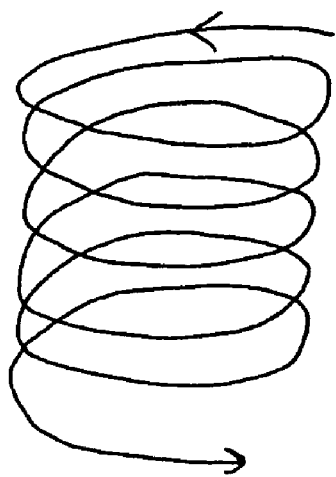
Figure 29:
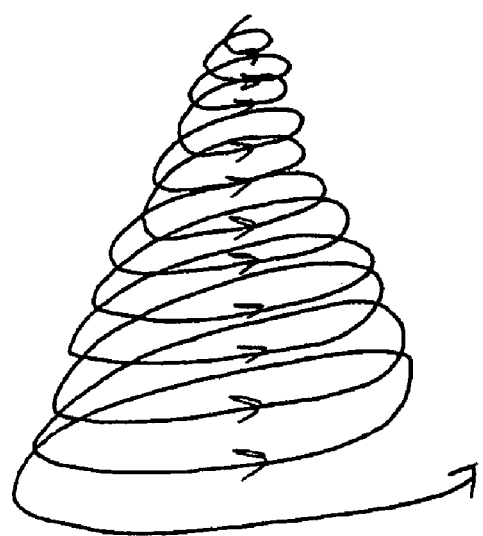

FIG. 26 depicts a tetrahedonal volume which is inspected in the manner of FIG. 25, however, the scale of the raster is varied as the probe is stepped along the axis orthogonal to the raster. In FIG. 27 an AMI probe is driven to contour scan a non-rectangular track-like area, and the process is repeated at progressively varied depths. FIG. 28 illustrates that the FIG. 27 volume can be inspected also by driving the probe in a helical locus of travel, much in the manner that a CNC controller drives a screw thread cutter. FIG. 29 is a variant of FIG. 28 wherein the radius of the helix is varied along the helix axis.

It is manifest from these few examples that with the present invention, efficient and rapid AMI inspection of areas and volumes of any describable shape can be performed. It is within the purview of the present invention that the motion controller (100 in FIG. 16) be programmed (with software, firmware, or hard wiring) to drive an acoustic probe to successively inspect independent 2D or 3D spaces within a sample volume. For example, in the FIG. 20 schematic illustration, if the location of the crack 136 were known, the motion controller 100 could direct the probe 134 to scan a 2D or 3D space encompassing the crack. If the location of the air bubble 138, occlusion 140 and disbond 142 were also known, the controller could be programmed to drive the probe to scan those regions in the most efficient scan mode. The favored scan mode would be chosen depending upon the shape and size of the defect, and other factors. Further, the controller 100 could be programmed to cause the inspections of these defects to be performed according to a predetermined sequence.

According to another aspect of the present invention, the process may be adaptive. As the reflectance or transmission data characterizing acoustic perturbations within the sample are collected in real time, the data may also be processed in real time to learn the location, configuration, impedance characteristics and other information about the perturbation. The information derived from processing the data can be employed to control the motion controller, either in real time or in future inspection of the same or other samples.

For example, if inspection of crack 136 develops data indicating that the crack is more extensive that previously predicted, the results of the processing function may be employed to revise the controller program to cause the controller to widen and/or deepen the initially programmed inspection region around the crack. Alternatively the motion controller could be programmed to respond to feedback from the received reflection signal in such a way that the probe locates the boundaries of the acoustic feature being inspected, determining its size, shape, and other features.

As another example of the adaptive nature of the methods and systems according to the invention, if upon inspection of air bubble 138 it is learned through real time or delayed processing of the reflectance or transmission data, that the bubble has an unpredicted characteristic, the controller may be programmed to also direct an inspection of air bubble 146 to learn whether that air bubble also has the same unpredicted characteristic of bubble 138.

As yet another example of the power of the invention, the controller (100 in FIG. 16) could be programmed to begin a conventional scan of a sample, but to immediately depart from the conventional scan and move the probe to another region if a certain perturbation or set of perturbations is detected. For example, in the inspection of the die pad bond element 180a, if a perturbation is found which qualifies as a defect, the controller could be programmed to immediately move the probe to bond elements 180b, 180c, and/or 180d.

The system according to the invention can include well-known artificial intelligence technology to enable the controller and its associated processing system to learn from inspection of certain types of samples where defects are most likely to be found, and to establish a prioritized inspection sequence of 2D or 3D spaces within the sample which are most likely to contain defects or other acoustic perturbations of interest.

Thus, it can be seen that application of the present invention offers greatly improved flexibility and efficiency, and greatly reduced processing time and resource utilization, as compared with the prior art process of scanning the entire volume containing the described defects.

The Motion Controller or Control System

Motion control systems suitable for implementing the principles of the invention are well known and commercially available today. A general review of available motion control system technology follows.

Motion control systems are typically used to coordinate motion between two or more axes, to coordinate or regulate speeds between axes or other machine members, to stimulate mechanical motions, or for rapid moves with high acceleration/deceleration rates. This precise control of position, speed, acceleration, and deceleration is typically achieved with a motor, drive, feedback device, motion controller, and control system or programmable logic controller (PLC).

The motor provides the actual motion. The feedback device provides position information from the motion device to the controller (so the controller can close the loop between the motion asked for and the actual motion made by the motor). The drive turns the command signal from the controller into usable current to drive the motor. The motion controller is responsible for closing the loop to the servo and accepting positioning requests from the control system or PLC.

Motion control systems provide positioning of a load, speed regulation, and acceleration rate control of servomotors, or stepper motors. Along with these control variables, motion control systems must provide axis data back to the controller through networking, synchronization of multiple moving machine members (axes), and processing of discrete or analog inputs or outputs.

Today, there are four primary types of motion control architectures: bus-based systems, stand-alone motion controllers, hybrid controllers, and PLC-based systems. Different implementations of the invention will find different architecture most suitable.

Bus-based systems use generic off-the-shelf hardware components and operating systems and combine them with proprietary custom-developed motion control applications. They provide high data-processing capability and are thus well suited for intensive communications. Bus-based systems (STD, VME, CompactPCI, IBM PC, ISA, IP and Multibus, for example) generally run on commercially available operating systems such as Wind River's Tornado, ISI's PsOS, Microsoft Windows, OS/2, or DOS.

In general, bus-based systems offer a lower hardware cost than other systems. Separate cards are required for motion, I/O, and communications requiring different software languages. Software determines the polling hierarchy of servo loops, motion operations, and I/O.

Typical use for bus-based systems includes simple, repeatable motion control on stand-alone original equipment manufacturer machines that need not be modified by the user or integrated with other equipment.

Stand-alone motion controllers have the controller, I/O, operator interface, and communications built into a single package. This integral architecture allows minimum development time and cost for typical machine applications. The servo-loop update, I/O, and operator interface are handled internally via proprietary software.

A single motion control software program simplifies application programming. While the initial hardware costs of motion controllers may be more expensive than bus-based systems, the total application cost may be lower due to decreased software, development, and maintenance investments. However, stand-alone motion controllers do not offer the same flexibility for communications and operator interfaces as bus-based control and are sometimes difficult to integrate into large-scale processes. Stand-alone motion controllers are often used for highly precise motion control with an integrated operator interface, where there is not much need for connection to other plant-floor equipment.

Hybrid motion controllers have a motion controller and servo drive controller packaged together and are configured for multiple controller/drive axes. Hybrid motion controllers offer the same advantages as stand-alone controllers, with a reduced cost for multiple axes. Velocity and position loops are fully digital, and because the loop tuning is stored in the motion controller, servo drive modules can be replaced without retuning. Along with the advantages of stand-alone motion controllers, hybrid motion controllers also can present decreased flexibility with I/O and operator interface and difficult integration for large-scale processes.

PLC-based motion control systems are acceptable for a wide range of motion applications. PLC-based controllers used for motion control incorporate a motion controller as a module in the PLC rack. Coarse motion planning along with I/O, operator interface, and communications are integrated into the PLC and communicated to a motion module plugged into the PLC backplane.

The motion controller then only needs to close the servo loop. The dedicated motion modules use a separate microprocessor for improved response time. Multi-axis control can be synchronized off a common system clock on the PLC backplane. Because there is a fairly large installed base of PLCs, motion control integration into large-scale processes can be a low-cost, high-performance option for many manufacturers.

Recent developments of motion control technology integrate the motion controller and the PLC, resulting in higher system performance, faster application development and integration, and easier maintenance. Performance is increased because the controller and motion module reside on the same hardware chassis, for faster communications than are possible over a multinode network.

On the component level, there are many types of electric motors which may be employed, each with its own power drive requirements. Three common types are alternating current (AC) servo motors, direct current (DC) servo motors, and stepper motors.

AC servo motors can be inexpensive to build and operate, are reliable, and usually operate at standard line voltages and frequencies. Since the speed of an AC motor is difficult to control, AC motors are most often used for simple motion rather than for sophisticated motion control applications.

DC servo motors operate from a direct current power source and are suited for complex motion tasks because the speed and torque (twisting force) in DC motors are controlled by varying the voltage and current.

Stepper motors produce motion in discrete steps. These motors have a specified number of steps per revolution, but more advanced stepper drives can provide microstepping-additional stops between the normal step locations. Microstepping greatly increases the resolution of the stepper motor.

The current and voltage that drives a motor typically comes from a power electronics device, known as an amplifier or drive. Power drives, located between the motion controller and the motor, take the control signals generated by the motion control board and convert them into power signals for the motor.

Most modern motion controllers use the power of the microprocessor to generate and execute complex motion profiles. These controllers are usually programmable, and programming is accomplished with hardware switch settings or keypads on the control board inside the PC or through some external computer with a communication link.

With programmable motion controllers, the user can input a motion profile and specify motor acceleration, maximum velocity, deceleration, and ending position for many successive moves. Controllers often provide the ability to add delays between moves, to wait for inputs from external digital signals, or to set digital outputs based on the motor's position.

A controller has four fundamental tasks: plan what to do, start doing it, monitor what is happening in the real world, and correct for errors. Closed-loop or servo controllers perform all four tasks. Open loop controllers perform only the first two functions and are used when the system parameters are well known, or where precise control is not critical.

An encoder monitors the real-world status of the motion. Encoders are mounted on the motor shaft or the load, and provide digital pulses as the shaft or load moves. Encoders are specified by lines per revolution or counts per revolution. Velocity is determined by measuring the frequency of the incoming pulses, and position is determined by counting the number of pulses that have occurred.

Two basic types of optical encoders exist—incremental and absolute position. Incremental encoders are the simpler devices. Their output is a series of square wave pulses generated as a code disk, with evenly spaced opaque radial lines on its surface, rotates past the light source. The number of lines on the disk determines the encoder's resolution.

Absolute position encoders are more complex and provide a unique output for every position. The code disk consists of multiple concentric tracks of opaque and clear segments. Each track is independent with its own photodetector to simultaneously read a unique disk position. The number of tracks corresponds to the binary bit resolution of the encoder. That is, for example, a 12-bit absolute encoder has 12 tracks.

The controller takes position data values from the encoder and compares these values to the calculated value. If the values are the same, the controller simply outputs the next planned point. However, if there is error, the controller compensates by adding to or subtracting from the output signal.

Sophisticated controllers depend heavily on software, not only for the low-level control calculations, but also for high-level user interaction. Graphical programming package such as LabVIEWS from National Instruments. LabVIEW virtual instruments (VIs) for motion control are available for most PC-based motion control boards.

Figure 30:
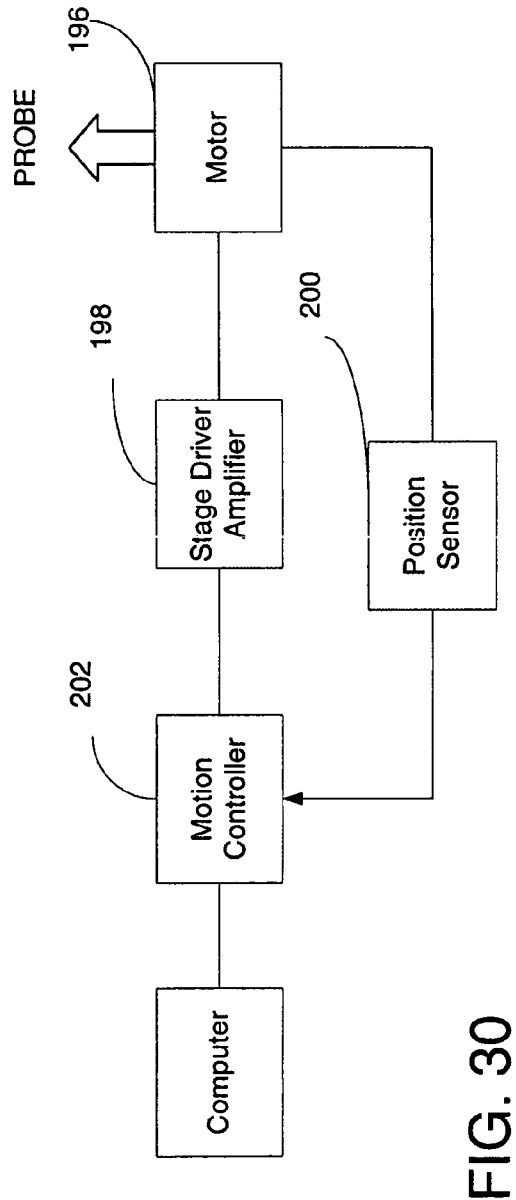
FIGS. 30–36 are schematic diagrams depicting motion controllers and motion control systems which may be used to implement the teachings of the present invention.
Figure 31:
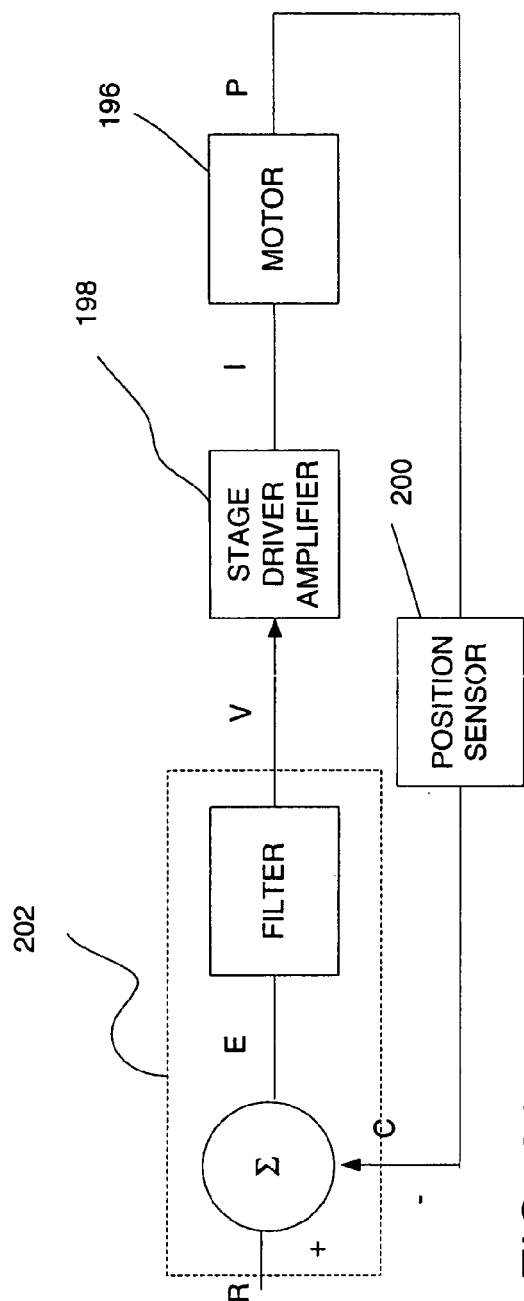

The elements of a motion control system, illustrated in FIG. 30, include a motor 196, an amplifier 198, a position sensor 200, and a controller 202. FIG. 31 shows the functional operation of these elements. Correlating with the FIG.

16 system—in FIG. 16 the motor (196 in FIG. 30) and position sensor (200 in FIG. 30) are part of stage 106. In FIGS. 16X-Y-Z stage driver 108 corresponds to amplifier 198 in FIG. 30, and motion controller 100 in FIG. 16 corresponds to motion controller 202 in FIG. 30.

Motor current is supplied by the driver or amplifier 204. This device produces a current I in proportion to the applied voltage V. Besides performing control functions, the controller generates the command signal to the amplifier. The position sensor 200, considered the eyes of the system, produces an output that is fed back to the controller. Many systems use optical encoders which generate electric pulses in proportion to the output rotation. By counting encoder pulses, the (incremental) encoder can figure out motor position.

Referring to FIG. 31, the controller 202 compares the position feedback signal C with input signal R to form the position error E. The error is then filtered in filter 204 (also part of the controller), producing a voltage signal V to drive the amplifier 198 which generates motor current I. The resulting change in motor position is measured by the sensor 200, and the process begins again.

Figure 32:
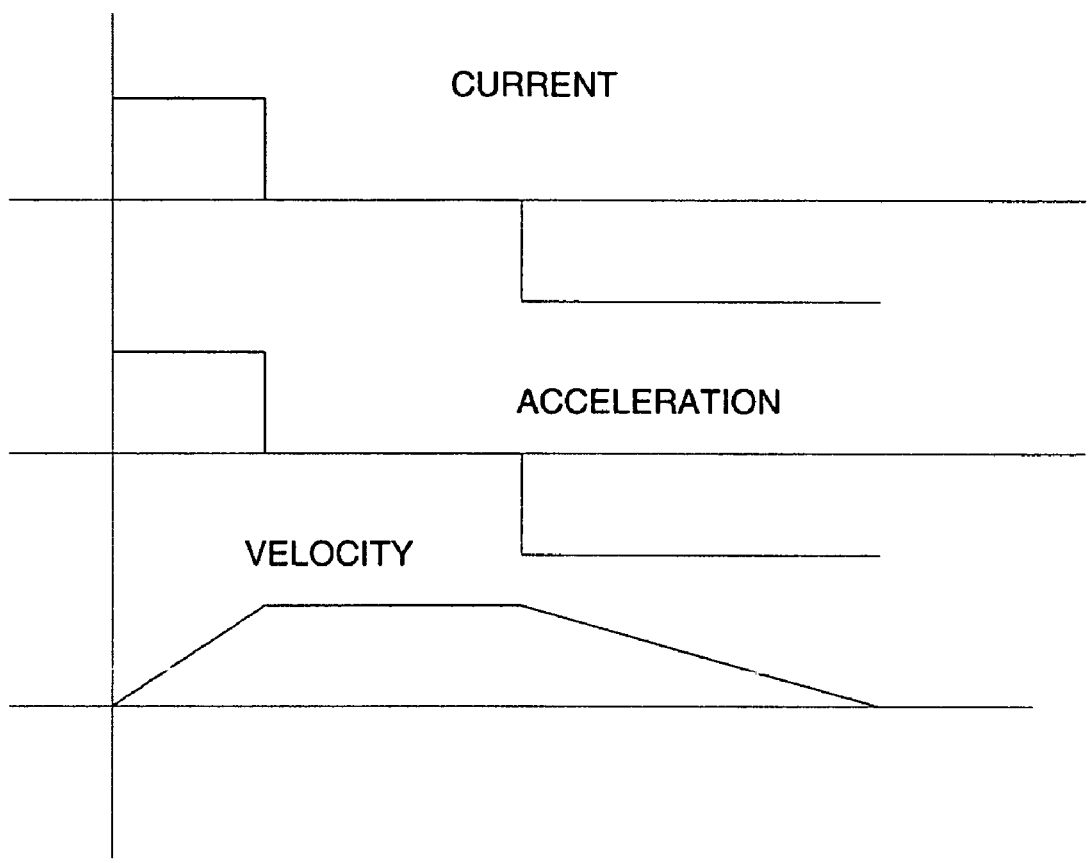

Assume a case where the motor is required to move along a trapezoidal velocity profile. FIG. 32 shows the corresponding velocity, acceleration, and motor current signals.

Filter parameters determine the intensity of the response of the controller, and therefore, the nature of the resulting motion, The most common filter is of a type called PID. The first parameter P determines the gain or intensity of the response, while D is associated with damping or stability, and I with accuracy.

Programming languages vary from one motion controller to another, but there are similarities. All languages specify velocity, acceleration, and distance, for example.

Many applications that incorporate an isolated motion component, such as an individual thrust cylinder, rotary actuator, or spindle, are adequately addressed using dedicated single-axis controllers. However, multi-axis control capability may provide significant economy for commanding the operations of numerous independent motion axes, and it is absolutely essential for coordinating the motion of elements in complex materials-working and spatial-measurement devices.

The term multi-axis control, referring to the ability to direct the operations of several motors in a system, applies to a variety of configurations. Hardwired multi-axis controls, though still acceptable for simple motion, have been supplanted by more adaptable microprocessor-based digital systems.

Figure 33:
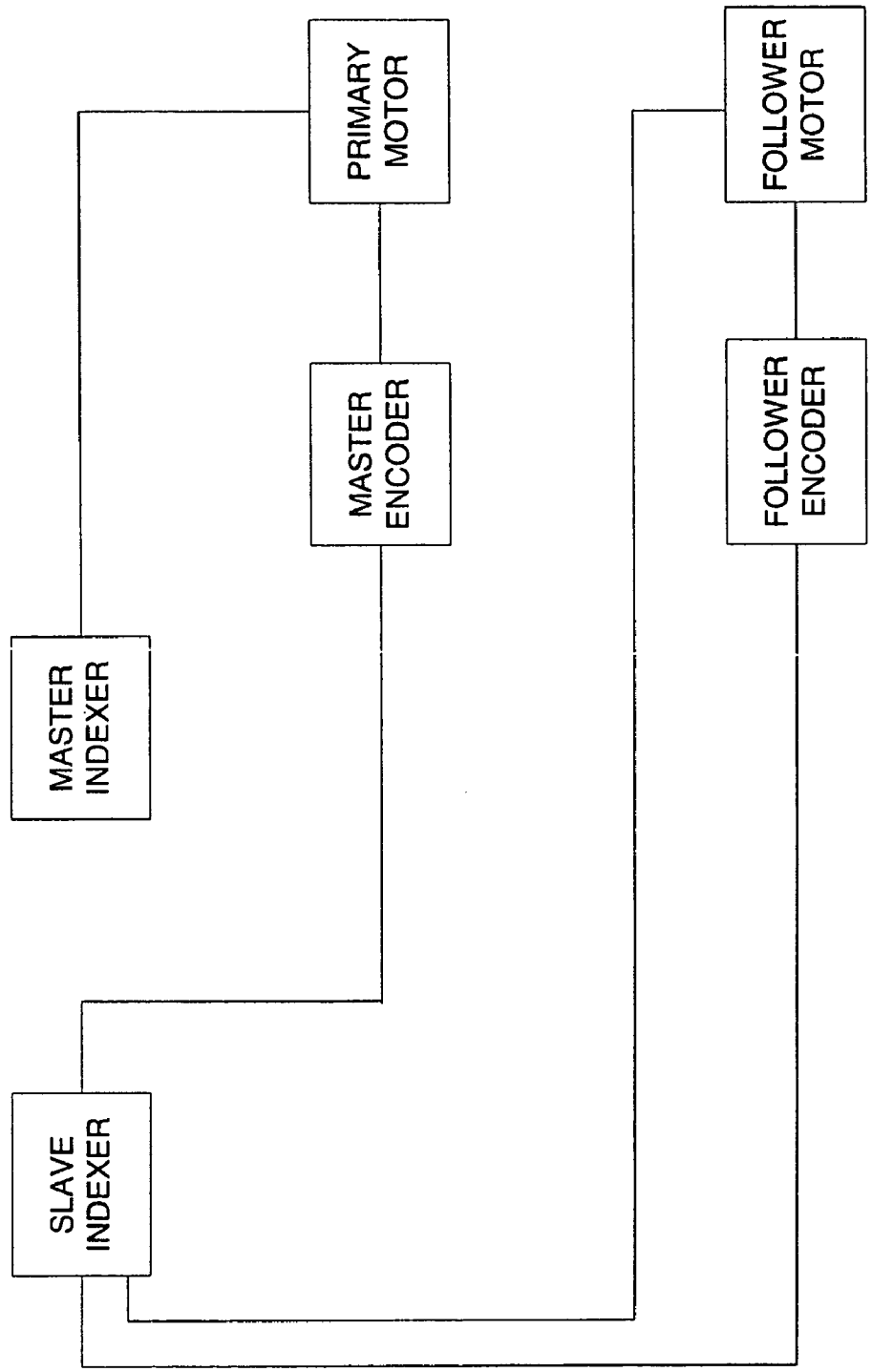

The simplest multi-axis device is the master/slave system (FIG. 33), in which the follower units accurately track the master at some velocity or positional ratio to provide the motion control equivalents of a gearbox and a cam mechanism.

Figure 34:
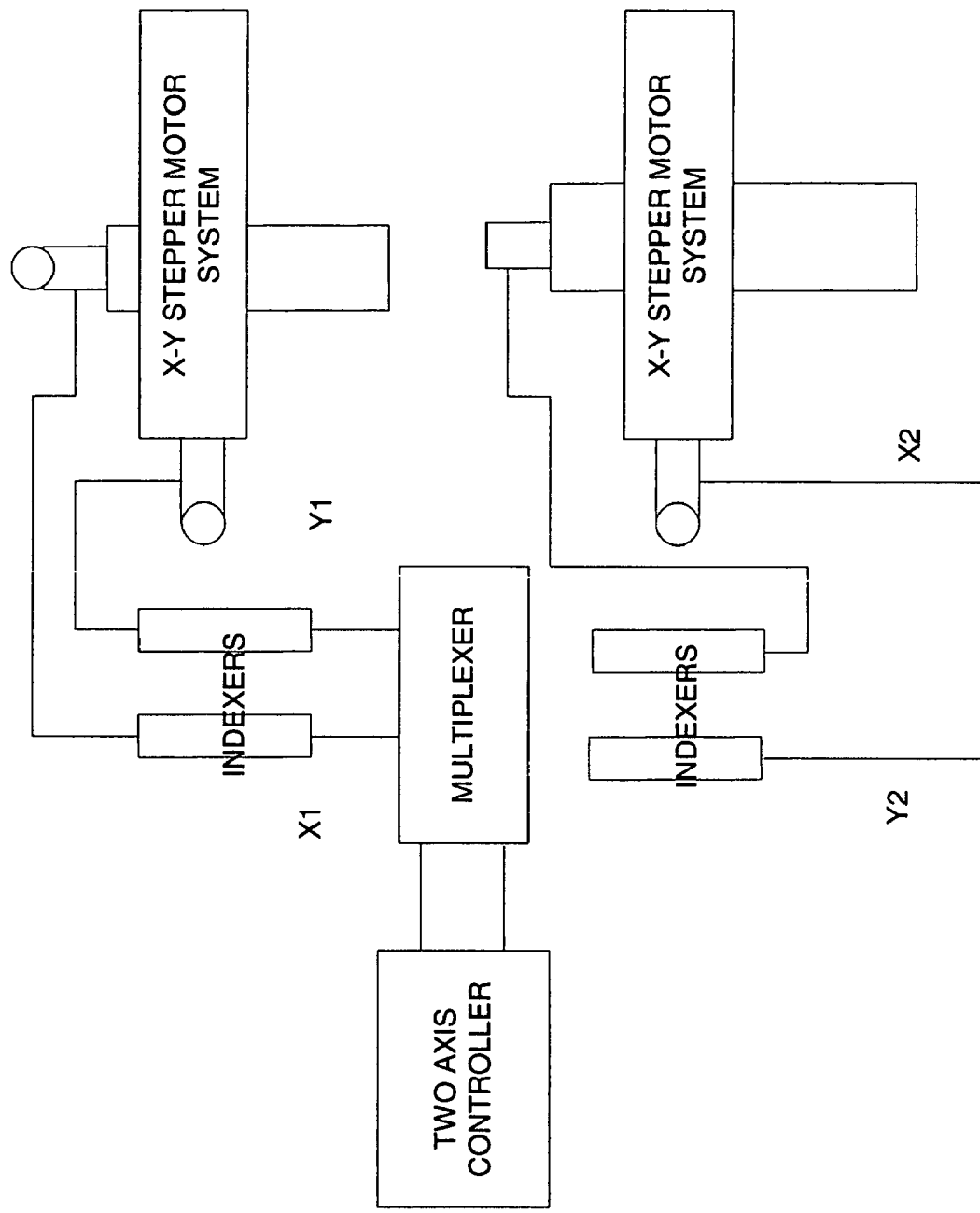

Multiplexing offers a degree-independent multi-axis operation via the switching of control authority among a number of motors in a time-sharing mode. While the technique is impractical for closed-loop operations, multiplexing is useful with steppers, provided that all motors in the system are not required to move simultaneously. In FIG. 34 a multiplexed two-axis control commands four motors in pairs to control two XY stations in a simple raster-scanning application.

Figure 35:
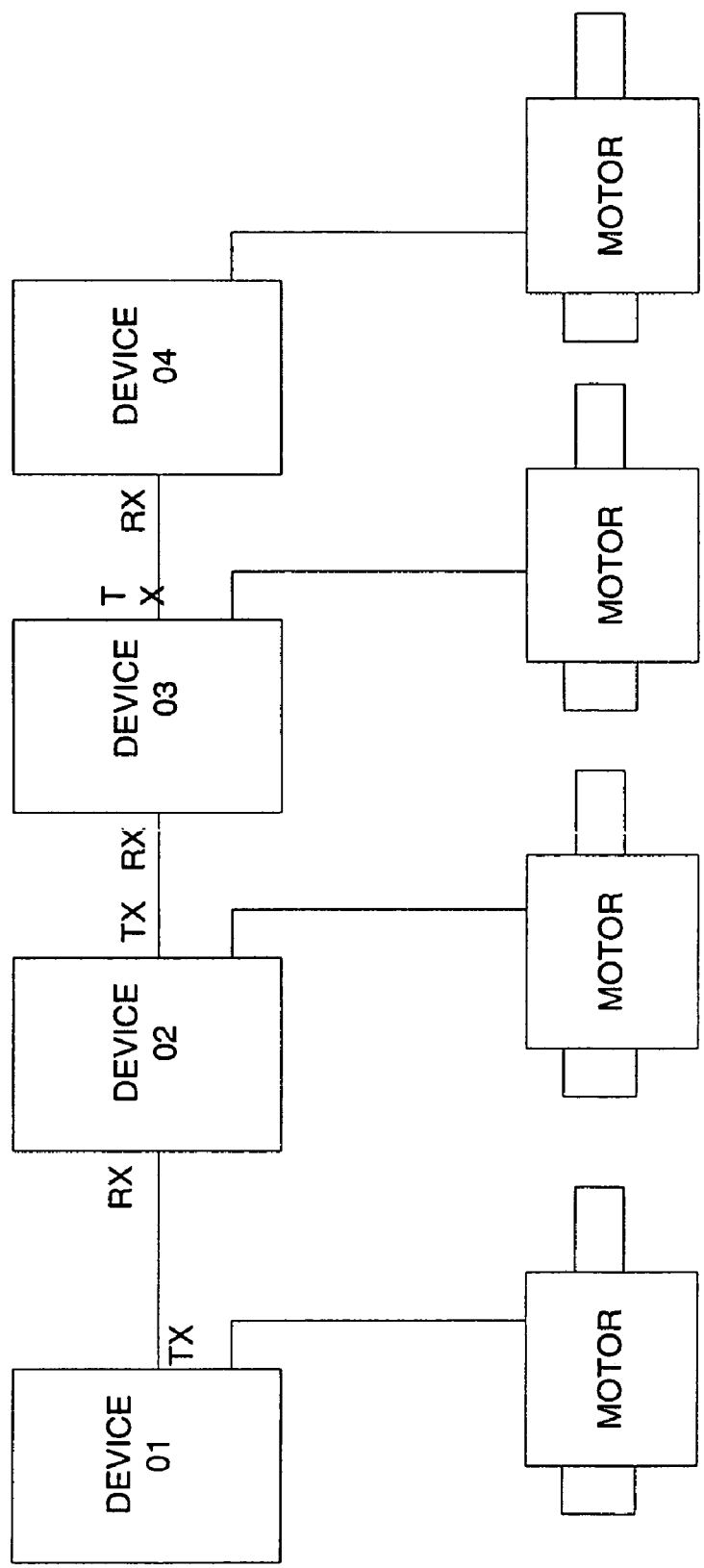

More capable multi-axis control involves daisy chaining. A daisy chain (FIG. 35) consists of several single-axis indexing devices that are serially connected (RS-232C, RS-422, RS-423, or RS-485) to provide a single data stream that flows through each to the next. Every device in the chain is assigned a unique address, which is referenced in the serial data to selectively activate each indexer as required.

Typical device addressing accommodates up to 99 motor indexers in the chain. Serial data-transmission rates and loading parameters to each indexer prior to move initiation limit daisy chaining to point-to-point displacement, where the intermediate path is not critical, and relatively low-speed applications, which do not require close coordination of the motion axes.

A similar degree of multi-axis capability may be achieved with groups of single-axis indexers coupled with a programmable logic controller (PLC). A PLC, which is designed and optimized for control of I/O-intensive applications, incorporates a processor that polls relay inputs and activates relay outputs in response to the inputs, as directed by its programming.

The PLC merely activates or deactivates the various motor indexers controlling the motion. These indexers may be circuit cards compatible with the PLC backplane architecture or devices using BCD communications. While the system is complicated by the indexer programming language, in addition to the PLC ladder logic, PLC polling rates are unencumbered by the motion control function, since each indexer incorporates its own processors. Widespread familiarity with PLC programming makes this an acceptable multi-axis control strategy for most motion applications.

Fully integrated machine controllers provide the highest levels of multi-axis motion capacity. All motion control functions, including I/O, user interface, motor commutation, servo-loop updating, path computation, and others, are implemented on a single hardware platform using a common programming language. A machine controller might be termed a motion control computer, since it generally incorporates mathematical and logical operations, conditional branching, subroutines, and interrupt capabilities.

Although the majority of multi-axis controllers support 4–8 motorized axes, a specialized digital signal processor (DSP) can provide up to 32 axes of coordinated motion on a single circuit board. DSP speeds of up to 100 MHz provide for generation and high rate execution of complex motion trajectories, which are difficult or impossible to implement using arrays of single-axis indexers.

Typically, several routines are preconfigured to simplify trajectory programming. Linear interpolation facilitates straight-line motion in Cartesian space by automatically calculating the individual axis motions to achieve the desired vector move profile (path velocity and acceleration/deceleration) between the origin and destination coordinates.

Circular interpolation allows points to be smoothly traversed by arced paths for which the user specifies the orientation plane, the radius of curvature, motion path profile, and direction of motion. Helical interpolation provides for rapid creation of spiral motion. The most versatile machine controllers offer the ability to generate arbitrary move paths.

Typically, the user specifies a series of time spans, along with a series of terminal positions/distances, for each axis at the end of each segment. Cubic spline paths are computed to connect the specified points and ensure that there are no motion-profile discontinuities at the path segment boundaries.

Sophisticated multi-axis controllers are capable of simultaneously executing several asynchronous PLC programs in background to the main motion program. In addition to controlling I/O relays, PLC programs may be employed to dynamically adjust gain parameters to provide adaptive servo control.

Figure 36:
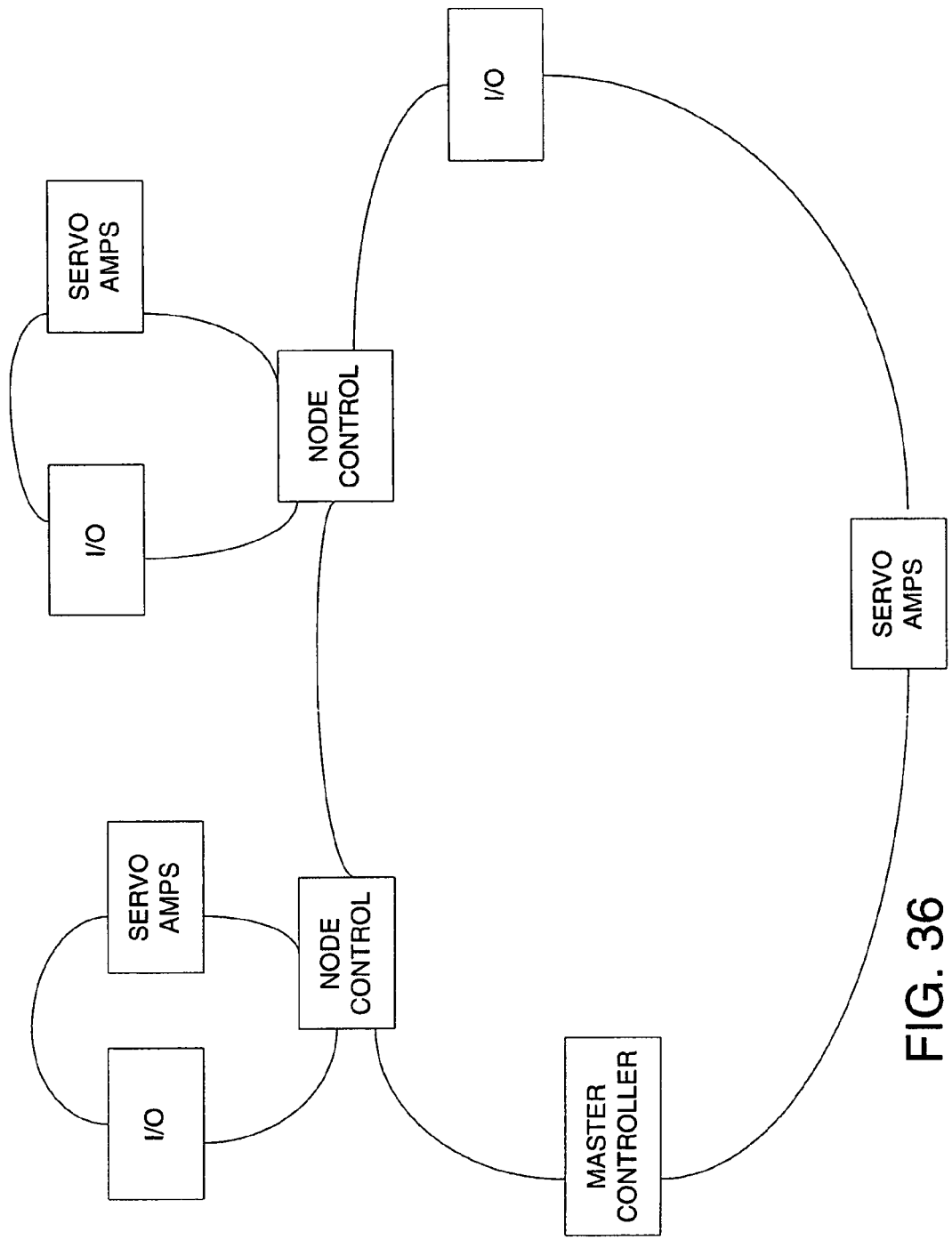

The latest development in multi-axis technology is the fiber-optic ring shown in FIG. 36. The ring is composed of a supervisory control and a number of nodes, which may include multi-axis controllers, serially communicating via glass fiber and optical transceivers at each device. SERCOS (SErial Real-Time COmmunication System) is the internationally approved open standard (IEC 61491) for synchronization of intelligent digital drives for multi-axis control.

While conceptually similar to the daisy chain described above, fiber optics eliminates many wire-circuit considerations (ground loops, parasitic capacitance, and so on), while simultaneously providing bandwidth (>100 Megabits/sec) sufficient to close multiple high-performance servo loops across the ring. State-of the-art fiber ring controls can typically support up to 256 nodes with spans of up to 3,000 meters between nodes, thus providing distributed/intelligent network architecture.

Currently, ring systems may be marginally more economical when implemented with twisted-pair copper-wire interconnections if the lower ring data update rates and node-to-node spacing of approximately 30 meters are acceptable to the particular application.

An example of a commercially available controller that may be employed to implement the present invention is the UNIDEX 500 PC-based controller sold by Aerotech, Inc. of Pittsburgh, Pa.

The UNIDEX 500 family of multi-axis motion controllers is offered in two bus formats: ISA and PCI. For each bus format, three models are offered: BASE, PLUS and ULTRA having different performance capabilities. The UNIDEX 500 is fully capable of performing intricate contouring and raster scanning as described above. The product is adapted for programming in multiple languages including native G-code or AeroBASIC™, C++, VisualBasic™ or LabVIEW™. Common software libraries, utilities, and MMI (man machine interface) software are offered.

The UNIDEX 500 controllers are built on the Motorola 56000 family of DSP controllers for fast servo loop and extensive motion control functionality. A wide range of options complement the UNIDEX 500 controllers, including pulses synchronized output functionality, I/O, encoder multipliers, packaged drive chassis, interconnect boards, and handwheel and joystick options.

UNIDEX 500 software architecture includes a Windows™ based MMI500 interface, and extensive DLL libraries. DLL ("dynamic link library") is a special file that stores conventional C and C++(or any other DLL-capable language) functions in a separate file to the main application 'EXE' file. The MMI500 software handles program execution and status updates, and utilizes the owner's proprietary command set that includes standard motion and flow control commands.

For creating the complex probe motions needed to execute the present invention, the UNIDEX 500's DLL interface can be employed to give access to a comprehensive set of functions that are used to command the UNIDEX 500. These functions can be integrated into C, Visual Basic or any software that provides for DLL function calls. The DLL includes an interpreter which enables the user to build a custom operator interface and still take advantage of the comprehensive and fully documented AeroBASIC command set as their primary motion language.

Basic motion is accomplished through the MMI500's built-in jog panel. Jog modes include both index mode (distance-based) and free run mode (velocity based).

The motion control capabilities of the UMDEX 500 may be utilized drive an XYZ AMI probe motion stage, or in certain applications, to drive a sample motion stage with the probe fixed. Utilizing the UNIDEX 500's position synchronized output function, the pulsing of the probe can be precisely coordinated with stage position or velocity. The pulse rate or power can be automatically adjusted whenever the motion system changes velocity, such as decelerating for corners or small radius arcs.

Additional UNIDEX 500 specifications include:

Axes—up to eight per card, including four axes of synchronized servo control and four axes of stepper motor control;

Axis Processor—80 MHz, DSP, expandable to 100 MHz;

Axis Loop Update Rate—62.5 microseconds per axis;

Position Modes—absolute, incremental, dynamic trajectory correction; Motion Types Independent—point-to-point incremental; target position or velocity; velocity profiles; time based; free run;

Coordinated—advanced queuing and deferred execution features for simultaneous command execution;

Interpolated—four axis linear interpolation; velocity profiling; corner rounding; circular interpolation of up to two axis pairs; helical;

Digitally Geared Motions—n:m gear ratio for master/slave operation;

Trajectory Adjustment—on-the-fly trajectory modification;

Advanced Features—automatic PID loop gain computation (auto tuning); high speed registration;

Acceleration Profiles—linear, modified sine and custom profiles (1 second to 32.768 seconds); and Programmable Multitasking—1 ms task execution and switch; up to 4 independent tasks.

Post Processing of Captured Data to Enhance Information Content

It is an aspect of the present invention to enhance by post processing the information content of the captured data, which, as described might be 2D or 3D, with or without additional A-scan data (an added dimension). In the FIG. 16 system block diagram, this function is performed in box 125 labeled "post process".

Figure 37:
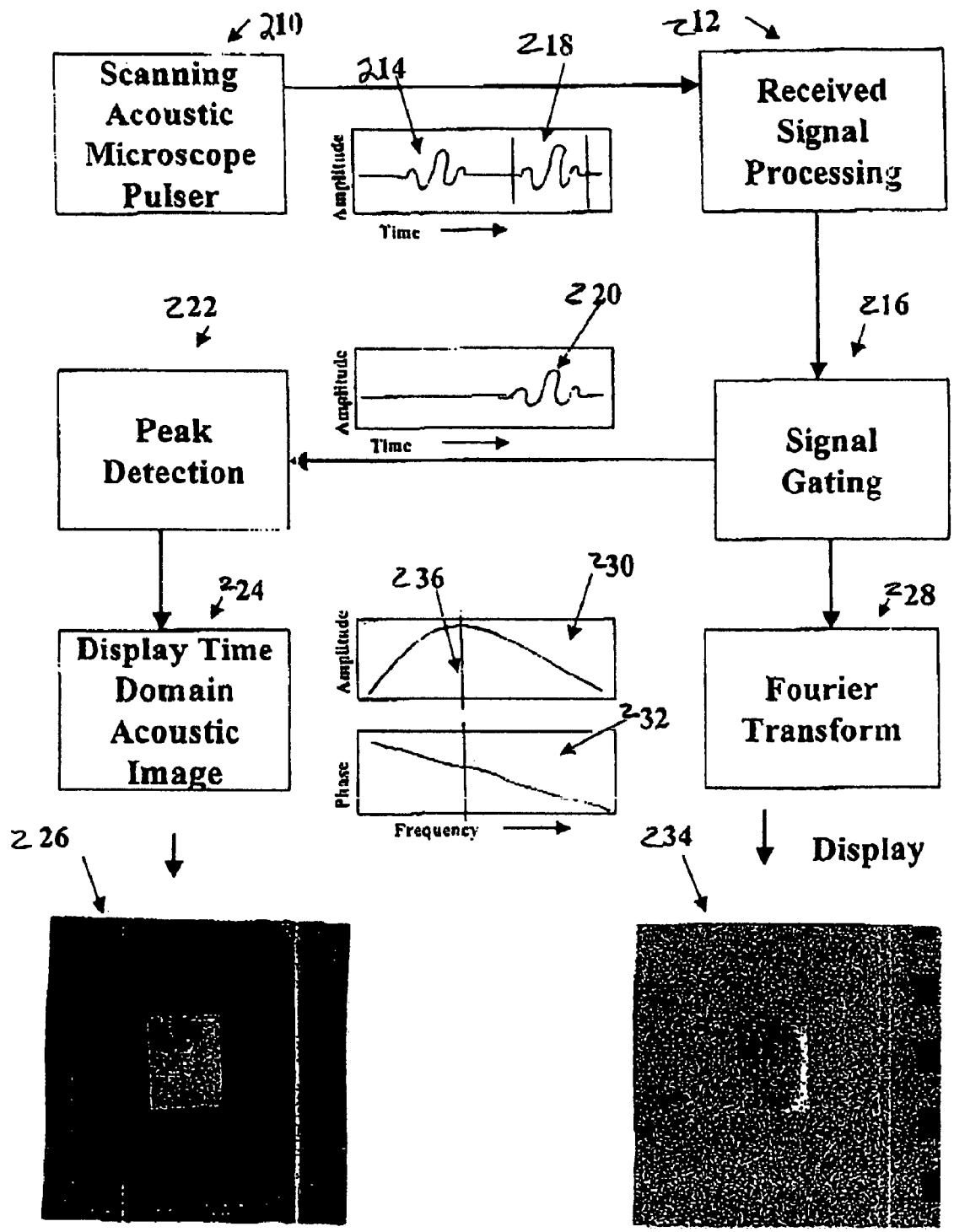
FIGS. 37–39 illustrate methods of post processing data acquired according to the present invention.

FIG. 37 is a schematic diagram illustrating a preferred execution of a method aspect of the invention adapted for processing 2D, 3D and 4D signals derived from a scanning acoustic microscope pulser 210. The pulser 210 in FIG. 37 corresponds to pulser 98 in the FIG. 16 system. The received signal processing 212 function is accomplished in receiver 110 and AGC 120 in the FIG. 16 system. The signal gating 216 and peak detection 222 in FIG. 37 corresponds to gate and detect 116 in FIG. 16. Fourier transform 228 represents one of many possible examples of post processing symbolized by box 125 in FIG. 16.

As is well known in the AMI art a scanning acoustic microscope typically comprises a transducer which is driven by sharp voltage pulses which may have amplitudes of 100 volts or more and are typically in the frequency range of tens of megahertz to 100 megahertz or higher.

The pulsed acoustic beam penetrates the target, which may be a medical or pharmaceutical package or an IC package, for example. As described at length above, a fraction of the energy passes through the target, and the remainder is absorbed or scattered. The return signal is an amplitude signal composed of a range of frequencies centered around the transducer's resonant frequency. FIG. 37 shows a receiver 212 adapted to sense and amplify the acoustic signal returned from the target. The time domain signal after processing by the receiver 212 has a waveform symbolized at 214. The time domain signal 214 is representative of amplitude variations in the returned acoustic pulses at the pixel level, or alternatively, the time domain signal 214 may represent a much longer gated segment of an A-scan. (See the description above for details of capture of AMI data in two or three spatial dimensions, plus a time dimension.).

The time domain signal 214 is conventionally gated by a gating process shown schematically at 216. During the gating process, a gate 218 isolates a pixel-representative signal segment associated with a single pixel, or longer-duration segment of an A-scan. The gated waveform illustrating only the gated segment of the signal 214 is shown at 220.

Gating of the signal permits the user to examine any chosen level in the target simply by selecting an appropriate delay time for the gate. For example, a single pixel segment might be captured with a gate 100 nanoseconds wide set at a delay of 384–484 nanoseconds. If a deeper level were to be visualized, a longer delay would be employed.

In accordance with standard practice in scanning acoustic microscopy, the gated pixel-wise signal segment 220 is subjected to a peak detection step 222 and then is displayed as a time domain acoustic image (see step 224 in FIG. 37). A standard time domain acoustic image is shown at 226. In the image at 226, the target is an IC package; the darkened area in the upper left corner indicates a disbond where the reflected acoustic energy is significantly higher than in the remaining areas of the target.

The present invention includes in one aspect a method of post processing a time-domain signal derived from an acoustic microscope. In a preferred execution, the post processing step includes converting the gated time domain signal to a frequency domain representation of the signal. More particularly, with reference to step 228 in FIG. 37, the gated output time domain signal segment 220 is subjected to a Fourier transform, fast Fourier transform, discrete Fourier transform or other such well known signal processing systems with windowing functions.

Two outputs may be developed by the Fourier transform step—an amplitude versus frequency waveform, sketched at 230, and a phase versus frequency waveform, sketched at 232.

In accordance with an aspect of the present method, an output from the Fourier transform step 228 is visually reproduced, as shown at 234. The information content of the frequency domain characterization of the pixels (one of which is under discussion here) is in many cases dramatically different from that produced by a time domain visualization. This can be noted even in the poorly reproduced pictures shown at 226 (time domain) and 234 (frequency domain). The pictures 26 and 34 are taken from successful laboratory tests.

It must be understood that the particular waveforms 220, 230 and 232 are each associated with a particular chosen pixel (or longer-duration gated signal A-scan segment), whereas the time domain image 226 and the frequency domain image 234 are images of the entire target or some macro portion thereof.

In accordance with the present invention, two methods are offered for selecting the frequency components of the signal which are to be visualized in the frequency domain representation. FIG. 37 depicts one of the methods wherein in the frequency domain waveforms 230, 232, a single frequency (indicated at 236 on waveform 230) is selected. This may be accomplished with Windows™ software which facilitates selection of the particular chosen frequency under the control of a mouse.

The particular frequency 236 selected may, for example, be at the peak of the pixel-wise amplitude versus frequency waveform 230 as shown. That selected frequency then becomes the frequency component which is visualized for all pixels in the display. Thus as the chosen frequency 236 is varied along the frequency axis of signal segment 220, the visual appearance of the image 234 may change dramatically, indicating that the acoustic reflections from the target may vary widely at a particular target depth with the particular frequency being studied.

The frequency domain information alone is proving to be very valuable in providing clues to hidden structures and anomalies within a target. By simultaneously displaying both time domain and frequency domain signals side by side or superimposed, still further information can be derived concerning the target internal structures and anomalies. This subject will be discussed further in connection with the method of FIG. 38.

The particular site on the target where the determinate pixel of interest is located is preferably determined through Windows™ software which places a cursor under mouse or keyboard control at any desired location on the target.

Figure 38:
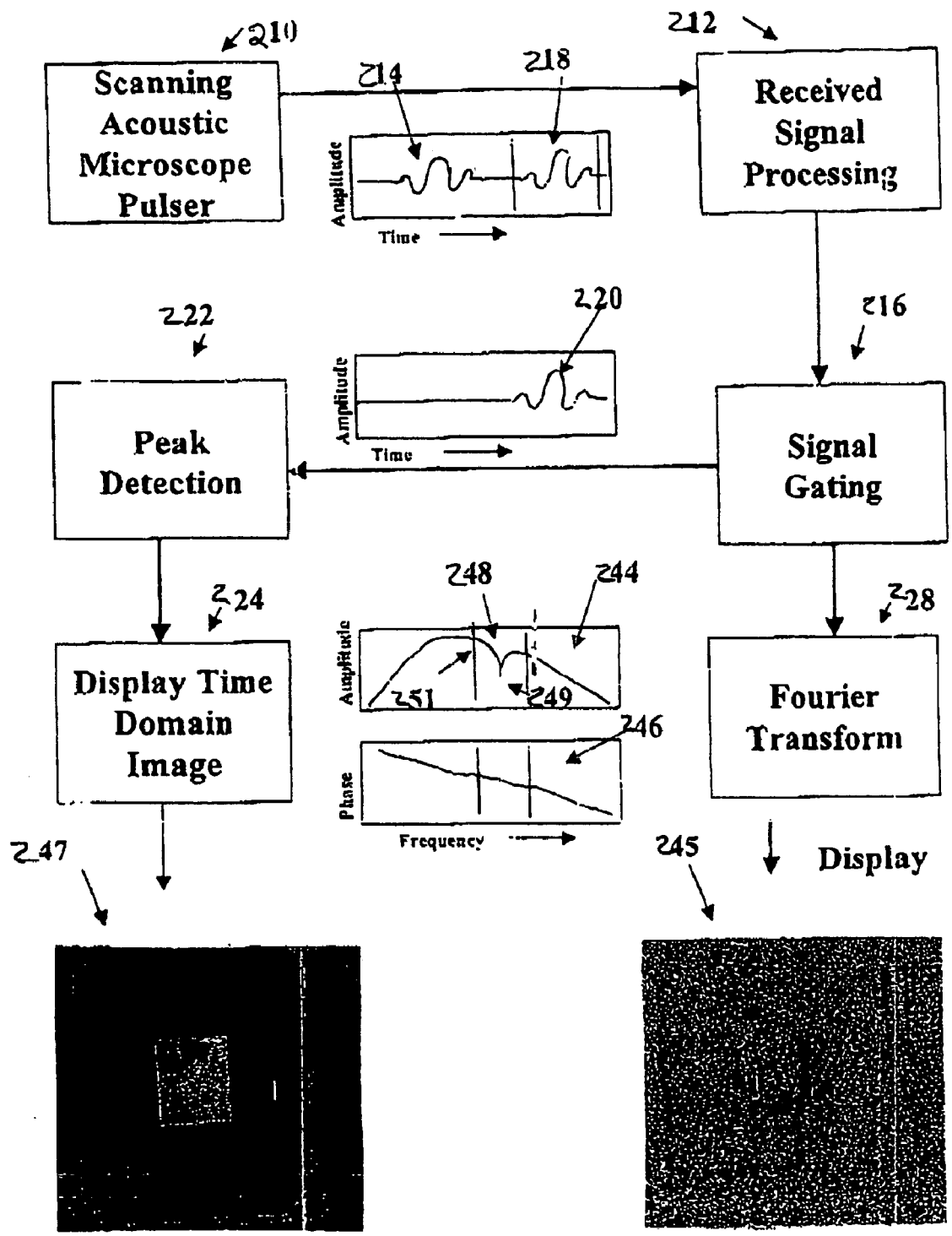

A second method of implementing the principles of the invention is depicted schematically in FIG. 38. It is noted that the same reference numerals appearing in different figures indicates like structure and function. Thus the FIG. 38 method may be the same as the FIG. 37 method described above except for the method step of selecting the frequency component of the frequency domain waveform to be visualized.

Again, as in the FIG. 37 method, the output of the Fourier transform step 228 may comprise an amplitude versus frequency waveform 244 and a phase versus frequency waveform 246. However, rather than selecting a single frequency to be visualized for the chosen pixel and all pixels (that is, image-wise), a band 248 of frequencies is selected. The width and location of the band on the waveform 244 is preferably varied using Windows™ software which permits under mouse or keyboard control, varying of the location and width of the band 248 delimiters.

Thus the user may choose at will the width and location of the band of frequencies to be visualized. He or she might be interested in embracing a range of frequencies across the peak of the amplitude versus frequency waveform. If the entire waveform is compressed at one end of the spectrum for example, the user may wish to embrace the entire band of frequencies. Having selected the band and its location, in accordance with a step of the present invention (not shown), an algorithm is chosen which will produce a single valued output in the application of the chosen band of frequencies to each pixel in the target to be processed and displayed. The algorithm may, for example, average the amplitudes of the frequencies in the band, or choose the lowest value in the band 48 (see point 49 on waveform 244) or the highest amplitude value in the band (see point 51 on the waveform 244).

The waveform 244 is illustrated as having a curious dip within the chosen band 248 of frequencies for the selected pixel. This is the type of information which likely would not be revealed in a rendition of a conventional peak-detected time domain signal. What might cause such a dip? If the target included two closely spaced and parallel interfaces reflected acoustic waves could interfere constructively and destructively. Interference would occur at certain frequencies and not at others. Thus the phenomenon is frequency selective.

With a broad band of reflected frequencies as normally occurs, the particular band or bands of frequencies affected, and the distances in the target corresponding to multiples of their wavelengths, could signify valuable interface spacing or other information. Thus the dip in the band 248 could signify that interference is occurring in the span of frequencies across the dip.

If one pixel or pixel group has a dip as described and an adjacent pixel or pixel group does not, this fact may be shown in an image-wise frequency domain display as an area of high contrast. The ability to visualize or otherwise develop information about a target's internal structure or anomalies which are undetectable using standard time domain imaging is one of advantages of Fourier transform signal processing according to the invention.

In FIG. 38, image 247 is a conventional time domain rendition of the target using conventional image processing as described. Image 245 is a frequency domain image produced using the Fourier domain conversion techniques described, and using a band of frequencies rather that a single frequency as in the FIG. 37 method. The visual differences in the two images are manifest, indicating the presence of new information in the frequency domain image than is not present in the time domain image.

Figure 39:
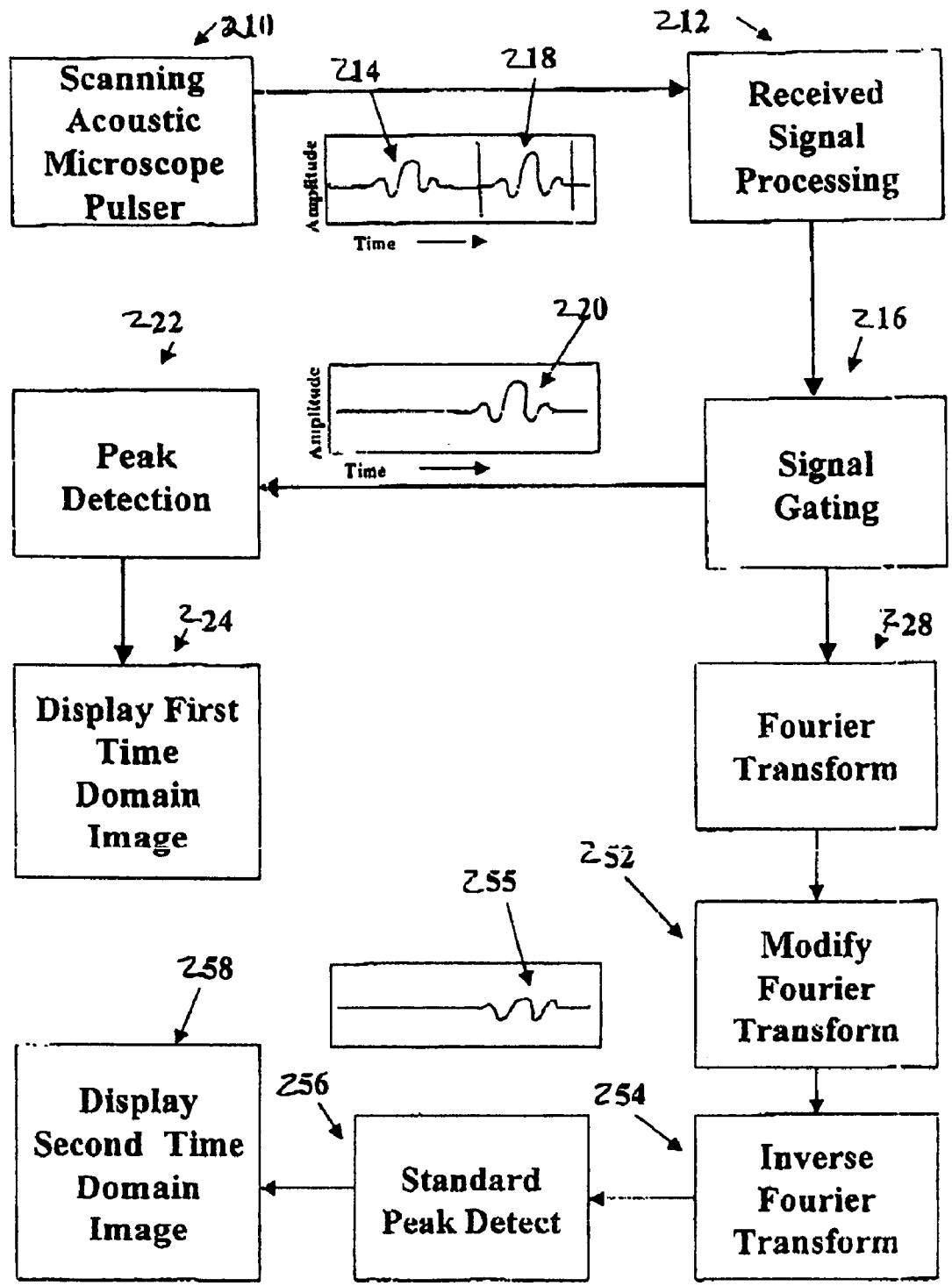

A third execution of the principles of the invention is depicted in FIG. 39, where again the use of like reference numerals denotes like structure and function. In the FIG. 39 execution, rather than processing and displaying the frequency domain output from the Fourier transform step 228 directly, its output is instead modified (step 252), as by any desired shading, apodizing or other filter function, for example, and then processed in an inverse Fourier transform step 254.

The output of the inverse Fourier transform step 254 is a gated time domain signal 255 which will have the general appearance of a gated time domain signal, but will differ from the gated time domain signal 220 derived from the pulser 210, receiver 212 and gating 216 steps, as a result of the predetermined filter function used to process the frequency domain characterization of the pixel signal.

Thus each of the three executions of the invention described operate on the frequency spectrum of an examined sample pixel—the first two methods by the selection for display of the frequency component (single frequency or band of frequencies). The FIG. 39 method contemplates a more sophisticated or aggressive (than simply gating) phase and/or amplitude filtering of the spectrum of frequencies in the return beam from the examined sample location.

Whereas the preferred executions of the described aspect of the invention have been in the context of Fourier transform processing of the derived acoustic signal, other processing functions may be applied.

While particular executions of the present invention have been shown and described, it will be obvious to those skilled in the art that other changes and modifications may be made without departing from the invention in its broader aspects. The appended claims are intended to cover all such changes and modifications that fall within the true spirit and scope of the invention. The matter set forth in the foregoing description and accompanying drawings is offered by way of illustration only and not as a limitation on the scope of the invention.

What is claimed is:

1. An apparatus for use in acoustic micro-imaging, said apparatus comprising:
    a transducer that is adapted to be coupled to a microelectronic sample or to a sealed package via a coupling medium;
    a controller that is operatively coupled to said transducer, said controller being adapted to cause said transducer to interrogate a space on a surface or within a volume of the microelectronic sample or the sealed package by emitting a pulse of acoustic energy toward each one of a plurality of points located within said space, and by receiving a reflection signal corresponding to each one of said emitted pulses;
    wherein said controller is further adapted to cause relative movement between said transducer and said microelectronic sample or the sealed package so that, when said space is being interrogated, said transducer follows one or more non-linear traces from a first-one of said points to a last one of said points;
    wherein all of said reflection signals represent acoustic impedance features present within said space so that, when a sealed package is interrogated by said transducer, the integrity of a seal defined in the sealed package can be inspected, and
    wherein said points are three-dimensionally varied within the microelectronic sample or sealed package.

2. The apparatus of claim 1, wherein said controller is further adapted to cause said transducer to have, for each one of said pulses, a focal point that is disposed at the same location within the given volume of the microelectronic sample or the package as the corresponding one of the three dimensionally varied points, and wherein each one of said reflection signals comprises an A-Scan of the microelectronic sample or the sealed package that is in-focus at the point within the given volume of the microelectronic sample or sealed package corresponding thereto.

3. The apparatus of claim 1, wherein said controller causes the microelectronic sample or the sealed package to be moved with respect to said transducer.

4. The apparatus of claim 1, wherein said non-linear trace comprises a spiral.

5. The apparatus of claim 1, further comprising a data memory that is operatively coupled to said controller and said transducer, said controller being adapted to cause digitized portions of each one of said reflection signals to be stored in said memory.

6. The apparatus of claim 5, wherein one or more of said digitized reflection signal contains both peak and at least some off-peak reflectance data.

7. The apparatus of claim 6, wherein one or more of said digitized reflection signals locations contains substantial all detectable portions of reflectance data.

8. The apparatus of claim 5, wherein said controller is adapted to retrieve selected ones of said digitized reflection signals and to create therefrom a composite digitized signal which represents an in-focus image of any impedance features at the points in the microelectronic sample or the sealed package that correspond to each selected one of said reflectance signals.

9. The apparatus of claim 8, wherein said controller is adapted to cause said composite digitized signal to stored in said memory.

10. The apparatus of claim 5, wherein said controller is adapted to combine two or more of said in-focus digitized reflection signals into an in-focus image at any location of interest within the microelectronic sample or the sealed package.

11. The apparatus of claim 5, farther comprising a display.

12. The apparatus of claim 11, wherein said controller is adapted to cause an in-focus representation of an impedance feature for an area of interest within the microelectronic sample or the sealed package to be displayed on said display.

13. The apparatus of claim 12, wherein said representation is in the form of a virtual sample volume or layer depicting an area of interest within the microelectronic sample or the sealed package.

14. The apparatus of claim 5, wherein said controller is adapted to alter a characteristic of said transducer selected from the group consisting of: pulse rate, pulse amplitude, pulse power, focal length, depth, and pulse bandwidth.

15. The apparatus of claim 1, wherein said space comprises a non-rectangularly bounded space.

16. The apparatus of claim 1, wherein said coupling medium comprises water.

* * * * *